(12) United States Patent
Matsuo et al.

(10) Patent No.: US 10,575,525 B2
(45) Date of Patent: Mar. 3, 2020

(54) BENZOXAZOLE COMPOUND OR SALT THEREOF, AGRICULTURAL AND HORTICULTURAL INSECTICIDE COMPRISING THE COMPOUND, AND METHOD FOR USING THE INSECTICIDE

(71) Applicant: Nihon Nohyaku Co., Ltd., Tokyo (JP)

(72) Inventors: Soichiro Matsuo, Osaka (JP); Ikki Yonemura, Osaka (JP); Akiyuki Suwa, Osaka (JP); Shunpei Fujie, Osaka (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 16/077,978

(22) PCT Filed: Feb. 24, 2017

(86) PCT No.: PCT/JP2017/007185
§ 371 (c)(1),
(2) Date: Aug. 14, 2018

(87) PCT Pub. No.: WO2017/146226
PCT Pub. Date: Aug. 31, 2017

(65) Prior Publication Data
US 2019/0045786 A1 Feb. 14, 2019

(30) Foreign Application Priority Data
Feb. 26, 2016 (JP) .................................. 2016-035044

(51) Int. Cl.
*A01N 43/76* (2006.01)
*C07D 413/14* (2006.01)
*C07D 413/04* (2006.01)
*A01N 47/02* (2006.01)
*A61K 31/4439* (2006.01)

(52) U.S. Cl.
CPC ............ *A01N 43/76* (2013.01); *A01N 47/02* (2013.01); *C07D 413/04* (2013.01); *A61K 31/4439* (2013.01)

(58) Field of Classification Search
USPC .................................................... 546/271.7
See application file for complete search history.

(56) References Cited

U.S. PATENT DOCUMENTS

| | | | |
|---|---|---|---|
| 10,005,766 B2* | 6/2018 | Miyamoto ........... | C07D 413/04 |
| 2008/0200528 A1 | 8/2008 | Koradin et al. | |
| 2011/0039843 A1 | 2/2011 | Iwakoshi et al. | |
| 2012/0015975 A1 | 1/2012 | Takahashi et al. | |
| 2012/0108586 A1 | 5/2012 | Iwakoshi et al. | |
| 2012/0178779 A1 | 7/2012 | Takahashi et al. | |
| 2012/0196891 A1 | 8/2012 | Iwakoshi | |
| 2012/0245167 A1 | 9/2012 | Iwakoshi et al. | |
| 2013/0190271 A1 | 7/2013 | Iwakoshi et al. | |
| 2013/0252981 A1 | 9/2013 | Takahashi et al. | |
| 2014/0018373 A1 | 1/2014 | Takyo et al. | |
| 2014/0194290 A1 | 7/2014 | Takahashi et al. | |
| 2014/0364444 A1 | 12/2014 | Takyo et al. | |
| 2015/0166573 A1* | 6/2015 | Takahashi ............... | A01N 43/76 514/252.04 |
| 2015/0197532 A1 | 7/2015 | Takahashi et al. | |
| 2015/0313234 A1* | 11/2015 | Takahashi ............ | C07D 263/57 424/40 |
| 2015/0366208 A1 | 12/2015 | Shimizu et al. | |
| 2016/0009715 A1 | 1/2016 | Takahashi et al. | |

(Continued)

FOREIGN PATENT DOCUMENTS

| | | |
|---|---|---|
| CA | 2939575 A1 | 8/2015 |
| CN | 103524422 A | 1/2014 |

(Continued)

OTHER PUBLICATIONS

Extended European Search Report for Application No. 17756660.1 dated Jun. 26, 2019.
International Search Report for PCT/JP2017/007185 dated Apr. 18, 2017.
International Preliminary Report on Patentability for PCT/JP2017/007185 dated Aug. 28, 2018.

*Primary Examiner* — Kamal A Saeed
(74) *Attorney, Agent, or Firm* — Knobbe, Martens, Olson & Bear, LLP

(57) ABSTRACT

In crop production in the fields of agriculture, horticulture and the like, the damage caused by insect pests etc. is still immense, and insect pests resistant to existing insecticides have emerged. To solve the problems, the present invention has been made, and an object of the present invention is to develop and provide a novel agricultural and horticultural insecticide.

The present invention provides a benzoxazole compound represented by the general formula (1):

[Chem. 1]

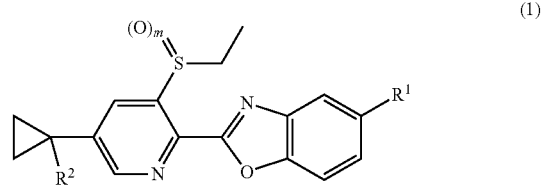

(1)

{wherein $R^1$ represents a trifluoromethoxy group or a trifluoromethylsulfinyl group, $R^2$ represents a hydrogen atom, and m represents 2}, or a salt thereof; an agricultural and horticultural insecticide comprising the compound or a salt thereof as an active ingredient; and a method for using the insecticide.

6 Claims, No Drawings

(56) References Cited

U.S. PATENT DOCUMENTS

| | | |
|---|---|---|
| 2016/0159743 A1 | 6/2016 | Takahashi et al. |
| 2016/0255837 A1 | 9/2016 | Edmunds et al. |
| 2016/0368915 A1 | 12/2016 | Tanabe et al. |
| 2017/0073342 A1 | 3/2017 | Fischer et al. |
| 2017/0233389 A1 | 8/2017 | Jung |
| 2018/0002347 A1 | 1/2018 | Yonemura et al. |
| 2019/0002451 A1* | 1/2019 | Sasayama ............ C07D 413/04 |

FOREIGN PATENT DOCUMENTS

| | | |
|---|---|---|
| EP | 2955178 A1 | 12/2015 |
| JP | 2009-280574 A | 12/2009 |
| JP | 2010-275301 A | 12/2010 |
| JP | 2011-79774 A | 4/2011 |
| JP | 2012-131780 A | 7/2012 |
| WO | WO 2006/128867 A1 | 12/2006 |
| WO | WO 2012/086848 A1 | 6/2012 |
| WO | WO 2013/018928 A1 | 2/2013 |
| WO | WO 2014/104407 A1 | 7/2014 |
| WO | WO 2014/119679 A1 | 8/2014 |
| WO | WO 2014/123205 A1 | 8/2014 |
| WO | WO 2015/000715 A1 | 1/2015 |
| WO | WO 2015/002211 A1 | 1/2015 |
| WO | WO 2015/121136 A1 | 8/2015 |
| WO | WO 2016/023954 A2 | 2/2016 |
| WO | WO 2016/121997 A1 | 8/2016 |

* cited by examiner

BENZOXAZOLE COMPOUND OR SALT THEREOF, AGRICULTURAL AND HORTICULTURAL INSECTICIDE COMPRISING THE COMPOUND, AND METHOD FOR USING THE INSECTICIDE

CROSS REFERENCE TO RELATED APPLICATIONS

This application is a U.S. National Phase Application of PCT International Application No. PCT/JP2017/007185, filed on Feb. 24, 2017, designating the United States of America and published in the Japanese language, which is an International Application of and claims the benefit of priority to Japanese Patent Application No. 2016-035044, filed on Feb. 26, 2016. The disclosures of the above-referenced applications are hereby expressly incorporated by reference in their entireties.

TECHNICAL FIELD

The present invention relates to an agricultural and horticultural insecticide comprising a condensed heterocyclic compound, particularly a benzoxazole compound, or a salt thereof as an active ingredient, and a method for using the insecticide.

BACKGROUND ART

Various compounds have been examined for their potential as agricultural and horticultural insecticides, and among them, certain kinds of condensed heterocyclic compounds have been reported to be useful as insecticides (for example, see Patent Literature 1 to 7). The literature, however, does not disclose any compound in which a cycloalkyl pyridyl group is bound to a benzoxazole compound.

CITATION LIST

Patent Literature

Patent Literature 1: JP-A 2009-280574
Patent Literature 2: JP-A 2010-275301
Patent Literature 3: JP-A 2011-79774
Patent Literature 4: JP-A 2012-131780
Patent Literature 5: WO 2012/086848
Patent Literature 6: WO 2013/018928
Patent Literature 7: WO 2015/121136

SUMMARY OF INVENTION

Technical Problem

In crop production in the fields of agriculture, horticulture and the like, the damage caused by insect pests etc. is still immense, and insect pests resistant to existing insecticides have emerged. Under such circumstances, the development of novel agricultural and horticultural insecticides is desired.

Solution to Problem

The present inventors conducted extensive research to solve the above-described problems. As a result, the present inventors found that a benzoxazole compound represented by the general formula (1) or a salt thereof is highly effective for the control of pests harmful to agriculture and horticulture, and reached the completion of the present invention.

That is, the present invention includes the following.
[1] A benzoxazole compound represented by the general formula (1):

[Chem. 1]

(1)

{wherein
R$^1$ 1represents a halo ($C_1$-$C_3$) alkoxy group; a halo ($C_1$-$C_3$) alkylsulfinyl group; or a halo ($C_1$-$C_3$) alkylsulfonyl group,
R$^2$ represents a hydrogen atom or a cyano group, and
m represents 0; 1; or 2}
or a salt thereof.
[2] The benzoxazole compound or the salt according to the above [1], wherein R$^1$ is a halo ($C_1$-$C_3$) alkoxy group.
[3] The benzoxazole compound or the salt according to the above [1], wherein R$^1$ is a halo ($C_1$-$C_3$) alkylsulfinyl group.
[4] An agricultural and horticultural insecticide comprising the benzoxazole compound or the salt according to any of the above [1] to [3] as an active ingredient.
[5] A method for using the agricultural and horticultural insecticide according to the above [4], the method comprising applying an effective amount of the benzoxazole compound or the salt according to any of the above [1] to [3] to plants or soil.
[6] An animal ectoparasite control agent comprising the benzoxazole compound or the salt according to any of the above [1] to [3] as an active ingredient.
[7] A condensed heterocyclic compound represented by the following formula:

[Chem. 2]

(1)

{wherein
R$^1$ represents
(a1) a halo ($C_1$-$C_3$) alkoxy group;
(a2) a halo ($C_1$-$C_3$) alkylsulfinyl group; or
(a3) a halo ($C_1$-$C_3$) alkylsulfonyl group,
R$^2$ represents
(b) a hydrogen atom or
(b2) a cyano group, and
m represents 0, 1, or 2}.
[8] The condensed heterocyclic compound according to the above [7], wherein R$^1$ is (a1) a halo ($C_1$-$C_6$) alkoxy group.
[9] The condensed heterocyclic compound according to the above [7], wherein R$^1$ is (a2) a halo ($C_1$-$C_6$) alkylsulfinyl group.

[10] An agricultural and horticultural insecticide comprising the condensed heterocyclic compound according to any of the above [7] to [9] as an active ingredient.

[11] A method for using an agricultural and horticultural insecticide, the method comprising applying an effective amount of the condensed heterocyclic compound according to any of the above [7] to [9] to plants or soil.

[12] An ectoparasite control agent comprising an effective amount of the condensed heterocyclic compound according to any of the above [7] to [9] as an active ingredient.

Advantageous Effects of Invention

The benzoxazole compound of the present invention or a salt thereof is not only highly effective as an agricultural and horticultural insecticide but also effective against pests which live on non-human animals including pets such as dogs and cats and domestic animals such as cattle and sheep.

DESCRIPTION OF EMBODIMENTS

In the definition of the benzoxazole compound represented by the general formula (1) of the present invention or a salt thereof, "halo" refers to a "halogen atom" and represents a fluorine atom, a chlorine atom, a bromine atom or an iodine atom.

The "halo $(C_1-C_3)$ alkoxy group" refers to a $(C_1-C_3)$ alkoxy group substituted with one or more halogen atoms at a substitutable position(s). In the case where a $(C_1-C_3)$ alkoxy group is substituted with two or more halogen atoms, the halogen atoms may be the same or different. Examples of the halo $(C_1-C_3)$ alkoxy group include a monofluoro methoxy group, a difluoro methoxy group, a trifluoro methoxy group, a 2,2,2-trifluoro ethoxy group, a 1,1,2,2-tetrafluoro ethoxy group, a perfluoro ethoxy group, a heptafluoro n-propoxy group and a heptafluoro isopropoxy group.

The "halo $(C_1-C_3)$ alkylsulfinyl group" refers to a $(C_1-C_3)$ alkylsulfinyl group substituted with one or more halogen atoms at a substitutable position(s). In the case where a $(C_1-C_3)$ alkylsulfinyl group is substituted with two or more halogen atoms, the halogen atoms may be the same or different. Examples of the halo $(C_1-C_3)$ alkylsulfinyl group include a monofluoro methylsulfinyl group, a difluoro methylsulfinyl group, a trifluoro methylsulfinyl group, a 2,2,2-trifluoro ethylsulfinyl group, a 1,1,2,2-tetrafluoro ethylsulfinyl group, a perfluoro ethylsulfinyl group, a heptafluoro n-propylsulfinyl group and a heptafluoro isopropylsulfinyl group.

The "halo $(C_1-C_3)$ alkylsulfonyl group" refers to a $(C_1-C_3)$ alkylsulfonyl group substituted with one or more halogen atoms at a substitutable position(s). In the case where a $(C_1-C_3)$ alkylsulfonyl group is substituted with two or more halogen atoms, the halogen atoms may be the same or different. Examples of the halo $(C_1-C_3)$ alkylsulfonyl group include a monofluoro methylsulfonyl group, a difluoro methylsulfonyl group, a trifluoro methylsulfonyl group, a 2,2,2-trifluoro ethylsulfonyl group, a 1,1,2,2-tetrafluoro ethylsulfonyl group, a perfluoro ethylsulfonyl group, a heptafluoro n-propylsulfonyl group and a heptafluoro isopropylsulfonyl group.

Examples of the salt of the benzoxazole compound represented by the general formula (1) of the present invention include inorganic acid salts, such as hydrochlorides, sulfates, nitrates and phosphates; organic acid salts, such as acetates, fumarates, maleates, oxalates, methanesulfonates, benzenesulfonates and p-toluenesulfonates; and salts with an inorganic or organic base such as a sodium ion, a potassium ion, a calcium ion and a trimethylammonium ion.

The benzoxazole compound represented by the general formula (1) of the present invention and a salt thereof can have one or more chiral centers in the structural formula, and can exist as two or more kinds of optical isomers or diastereomers. All the optical isomers and mixtures of the isomers at any ratio are also included in the present invention.

In a preferable embodiment of the benzoxazole compound represented by the general formula (1) of the present invention or a salt thereof, $R^1$ is a halo $(C_1-C_3)$ alkoxy group or a halo $(C_1-C_3)$ alkylsulfinyl group, $R^2$ is a hydrogen atom, and m is 2.

More preferably, $R^1$ is a halo $(C_1-C_3)$ alkylsulfinyl group, $R^2$ is a hydrogen atom, and m is 2.

The benzoxazole compound of the present invention or a salt thereof can be produced according to, for example, the production methods described below, which are non-limiting examples.

Production Method 1

[Chem. 3]

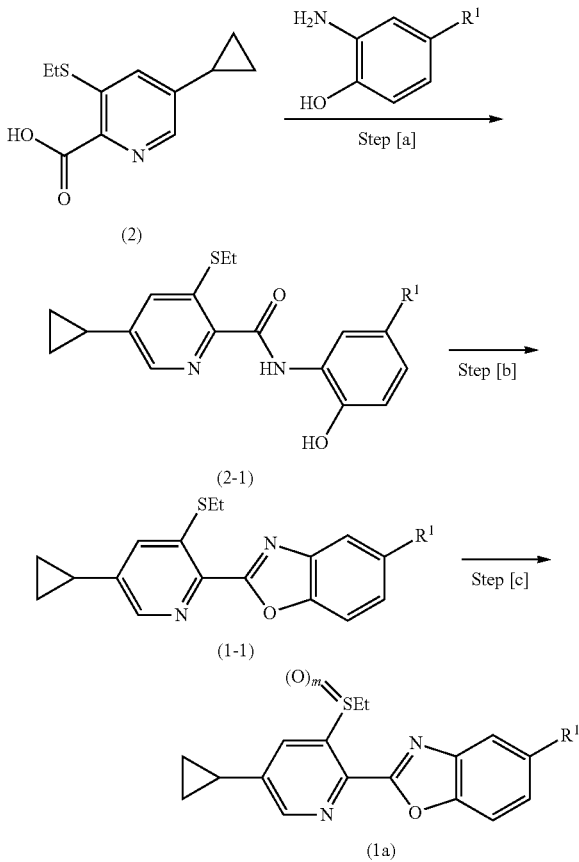

In the formula, $R^1$ is as defined above, and m represents 1 or 2.

The benzoxazole compound represented by the general formula (1a) of the present invention can be produced through the steps [a] to [c] described below.

Step [a]

A step of reacting the compound represented by the general formula (2) with an aminophenol compound, for producing the compound represented by the general formula (2-1).

Step [b]

A step of intramolecularly cyclizing the compound represented by the general formula (2-1), for producing the compound represented by the general formula (1-1).

Step [c]

A step of oxidizing the compound represented by the general formula (1-1), for producing the benzoxazole compound represented by the general formula (1a).

Production Method at Step [a]

The compound represented by the general formula (2-1) can be produced by reacting a carboxylic chloride produced from the compound of the general formula (2) in the usual manner of organic synthesis, with an aminophenol compound, which is commercially available and easily obtainable, in the presence of a base and an inert solvent.

Examples of the base that can be used in this reaction include inorganic bases such as sodium hydroxide, potassium hydroxide, sodium carbonate, potassium carbonate, sodium hydrogen carbonate and potassium hydrogen carbonate; alkali metal hydrides such as sodium hydride and potassium hydride; acetates such as potassium acetate; alkali metal alkoxides such as potassium t-butoxide, sodium methoxide and sodium ethoxide; tertiary amines such as triethylamine, diisopropylethylamine and 1,8-diazabicyclo[5.4.0]undec-7-ene; and nitrogen-containing aromatic compounds such as pyridine and dimethylaminopyridine. The amount of the base used is usually in the range of a 1- to 10-fold molar amount relative to the carboxylic chloride derived from the compound represented by the general formula (2).

The inert solvent used in this reaction may be any solvent that does not markedly inhibit the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide and 1,3-dimethyl-2-imidazolidinone. One of these inert solvents may be used alone, and also two or more of them may be used as a mixture. The amount of the inert solvent used is usually selected as appropriate from the range of 0.1 to 100 L relative to 1 mol of the carboxylic chloride derived from the compound represented by the general formula (2).

Since this reaction is an equimolar reaction of the reactants, they are basically used in equimolar amounts, but either of them may be used in an excess amount. The reaction temperature is usually in the range of room temperature to the boiling point of the inert solvent used. The reaction time varies with the reaction scale and the reaction temperature, but is usually in the range of a few minutes to 48 hours. After the reaction is completed, the compound of interest is isolated from the post-reaction mixture by the usual method. As needed, recrystallization, column chromatography, etc. can be employed for the purification of the compound of interest.

Production Method at Step [b]

The compound represented by the general formula (1-1) can be produced from the compound represented by the general formula (2-1) in the presence of an inert solvent according to the method described in Synthesis 1981, 1-28 (preferably using azodicarboxylic acid diester and triphenylphosphine ($PPh_3$)).

Production Method at Step [c]

The benzoxazole compound represented by the general formula (1a) can be produced by reacting the compound represented by the general formula (1-1) with an oxidizing agent in an inert solvent.

Examples of the oxidizing agent used in this reaction include peroxides such as a hydrogen peroxide solution, perbenzoic acid and m-chloroperoxybenzoic acid. The amount of the oxidizing agent used is usually selected as appropriate from the range of a 1- to 5-fold molar amount relative to the compound represented by the general formula (1-1).

The inert solvent used in this reaction may be any solvent that does not markedly inhibit the reaction, and the examples include straight-chain or cyclic ethers such as diethyl ether, tetrahydrofuran and dioxane; aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; organic acids such as formic acid and acetic acid; and polar solvents such as N,N-dimethylformamide, N,N-dimethylacetamide, 1,3-dimethyl-2-imidazolidinone and water. One of these inert solvents may be used alone, and also two or more of them may be used as a mixture. The amount of the inert solvent used is usually selected as appropriate from the range of 0.1 to 100 L relative to 1 mol of the compound represented by the general formula (1-1).

The reaction temperature is usually selected as appropriate from the range of −10° C. to the reflux temperature of the inert solvent used. The reaction time varies with the reaction scale, the reaction temperature and the like and is not the same in every case, but is usually selected as appropriate from the range of a few minutes to 48 hours. After the reaction is completed, the compound of interest is isolated from the post-reaction mixture by the usual method. As needed, recrystallization, column chromatography, etc. can be employed for the purification of the compound of interest.

Production Method of Intermediate (2')

[Chem. 4]

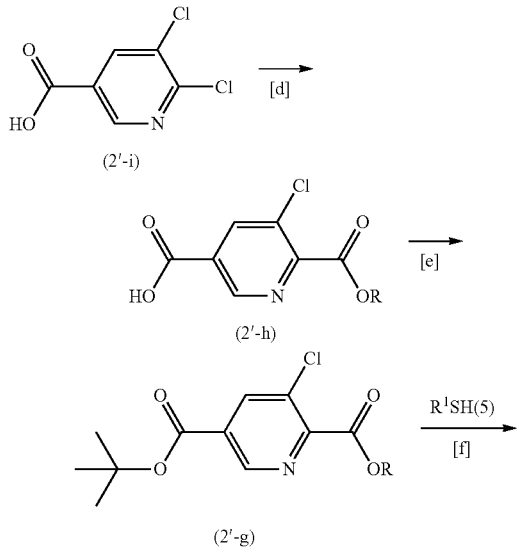

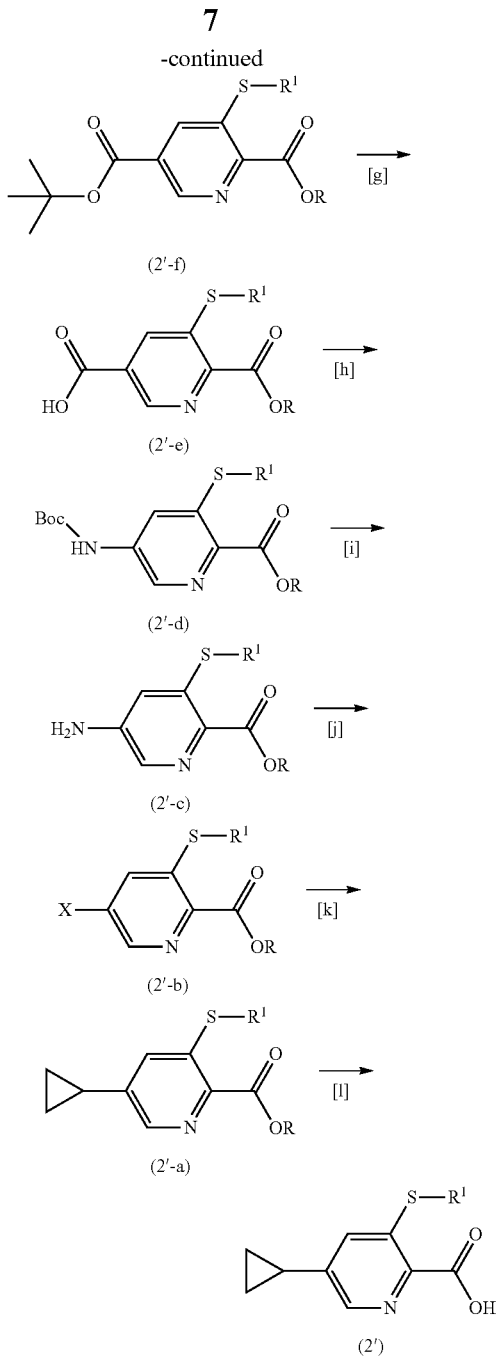

In the formula, $R^1$ is as defined above, Boc represents a tert-butoxycarbonyl group, R represents a $(C_1-C_3)$ alkyl group, and X represents a halogen atom. The "$(C_1-C_3)$ alkyl group" refers to a methyl group, an ethyl group, a n-propyl group or an isopropyl group.

The compound of the general formula (2'), which is an intermediate in the course of the production of the compound of the present invention, can be produced through the steps [d] to [l] described below.

Step [d]

A step of converting the halogen atom at the C-2 position of the dichloro pyridine carboxylic acid (2'-i) to an ester group, for producing the compound represented by the general formula (2'-h).

Step [e]

A step of protecting the carboxyl group of the compound represented by the general formula (2'-h) by tert-butyl esterification, for producing the compound represented by the general formula (2'-g).

Step [f]

A step of reacting the compound represented by the general formula (2'-g) with the compound represented by the general formula (5), for producing the compound represented by the general formula (2'-f).

Step [g]

A step of deprotecting the carboxyl group protected by tert-butyl esterification in the compound represented by the general formula (2'-f), for producing the compound represented by the general formula (2'-e).

Step [h]

A step of subjecting the compound represented by the general formula (2'-e) to the Curtius rearrangement, for producing the compound represented by the general formula (2'-d).

Step [i]

A step of removing the Boc protecting group for the amino group of the compound represented by the general formula (2'-d), for producing the compound represented by the general formula (2'-c).

Step [j]

A step of converting the amino group of the compound represented by the general formula (2'-c) to a halogen atom via the Sandmeyer reaction, for producing the compound represented by the general formula (2'-b).

Step [k]

A step of converting the halogen atom of the compound represented by the general formula (2'-b) to a cyclopropyl group via a cross-coupling reaction, for producing the compound represented by the general formula (2'-a).

Step [l]

A step of hydrolyzing the ester group of the compound represented by the general formula (2'-a), for producing the intermediate represented by the general formula (2').

Step [d]

The compound represented by the general formula (2'-h) can be produced by subjecting the dichloro pyridine carboxylic acid (2'-i), which is commercially available, to the reaction as described in JP-A 2005-272338.

Step [e]

By reacting the compound represented by the general formula (2'-h) with a chlorinating agent etc. in the presence of an inert solvent, the corresponding carboxylic chloride can be produced.

Examples of the inert solvent used in this reaction include ethers such as tetrahydrofuran (THF), ethylene glycol dimethyl ether, tert-butyl methyl ether and 1,4-dioxane; aromatic hydrocarbons such as toluene and xylene; halogenated hydrocarbons such as dichloromethane and chloroform; and a mixture thereof. The amount of the inert solvent used is usually selected as appropriate from the range of 0.1 to 100 L relative to 1 mol of the compound represented by the general formula (2'-h).

Examples of the chlorinating agent used in this reaction include thionyl chloride and oxalyl dichloride. The amount of the chlorinating agent used is usually in the range of a 1- to 10-fold molar amount relative to the compound represented by the general formula (2'-h). The reaction temperature is usually in the range of 0 to 100° C. The reaction time is usually in the range of 0.1 to 24 hours. After the completion of the reaction, the solvent, the excess chlorinating agent, etc. are evaporated off to give the desired carboxylic chloride.

The compound represented by the general formula (2'-g) can be produced by reacting the carboxylic chloride obtained from the compound represented by the general formula (2'-h) with a tert-butyl alcohol in the presence of a base and an inert solvent.

Examples of the solvent used in this reaction include ethers such as THF, ethylene glycol dimethyl ether, tert-butyl methyl ether and 1,4-dioxane; aromatic hydrocarbons such as toluene and xylene; halogenated hydrocarbons such as dichloromethane and chloroform; and a mixture thereof. The amount of the inert solvent used is usually selected as appropriate from the range of 0.1 to 100 L relative to 1 mol of the carboxylic chloride.

Examples of the base used in this reaction include inorganic bases such as sodium hydroxide, potassium hydroxide, sodium carbonate, potassium carbonate, sodium hydrogen carbonate and potassium hydrogen carbonate; acetates such as sodium acetate and potassium acetate; alkali metal alkoxides such as potassium t-butoxide, sodium methoxide and sodium ethoxide; tertiary amines such as triethylamine, diisopropylethylamine and 1,8-diazabicyclo[5.4.0]undec-7-ene; and nitrogen-containing aromatic compounds such as pyridine and dimethylaminopyridine. The amount of the base used is usually in the range of a 1- to 10-fold molar amount relative to the carboxylic chloride.

Step [f]

The compound represented by the general formula (2'-f) can be produced by reacting the compound represented by the general formula (2'-g) with the compound represented by the general formula (5) in the presence of an inert solvent.

Examples of the base used in this reaction include inorganic bases such as sodium hydroxide, potassium hydroxide, sodium carbonate, potassium carbonate, sodium hydrogen carbonate and potassium hydrogen carbonate; acetates such as sodium acetate and potassium acetate; alkali metal alkoxides such as potassium t-butoxide, sodium methoxide and sodium ethoxide; tertiary amines such as triethylamine, diisopropylethylamine and 1,8-diazabicyclo[5.4.0]undec-7-ene; and nitrogen-containing aromatic compounds such as pyridine and dimethylaminopyridine. The amount of the base used is usually in the range of a 1- to 10-fold molar amount relative to the compound represented by the general formula (2'-g). In the case where an alkali metal salt of the compound represented by the general formula (5) is used, it is not necessary to use a base.

The inert solvent used in this reaction may be any solvent that does not markedly inhibit the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide and 1,3-dimethyl-2-imidazolidinone. One of these inert solvents may be used alone, and also two or more of them may be used as a mixture. The amount of the inert solvent used is usually selected as appropriate from the range of 0.1 to 100 L relative to 1 mol of the compound represented by the general formula (2'-g).

Since this reaction is an equimolar reaction of the reactants, the compound represented by the general formula (5) and the compound represented by the general formula (2'-g) are used basically in equimolar amounts, but either of them may be used in an excess amount. The reaction temperature is in the range of −10° C. to the boiling point of the inert solvent used. The reaction time varies with the reaction scale and the reaction temperature, but is usually in the range of a few minutes to 48 hours. After the reaction is completed, the compound of interest is isolated from the post-reaction mixture by the usual method. As needed, recrystallization, column chromatography, etc. can be employed for the purification of the compound of interest.

Step [g]

The compound represented by the general formula (2'-e) can be produced by allowing the compound represented by the general formula (2'-f) to react in the presence of an acid and/or an inert solvent.

Examples of the acid used in this reaction include inorganic acids such as hydrochloric acid, sulfuric acid and nitric acid; organic acids such as formic acid, acetic acid, propionic acid, trifluoroacetic acid and benzoic acid; and sulfonic acids such as methanesulfonic acid and trifluoromethanesulfonic acid. The amount of the acid used is usually selected as appropriate from the range of a 1- to 10-fold molar amount relative to the compound represented by the general formula (2'-f). In some cases, the acid can be used to serve as the solvent as well.

The inert solvent used in this reaction may be any solvent that does not markedly inhibit the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide and 1,3-dimethyl-2-imidazolidinone. One of these inert solvents may be used alone, and also two or more of them may be used as a mixture. The amount of the inert solvent used is usually selected as appropriate from the range of 0.1 to 100 L relative to 1 mol of the compound represented by the general formula (2'-f). In the case where the acid is used as the solvent, it is not necessary to use another solvent.

The reaction temperature is usually in the range of room temperature to the boiling point of the inert solvent used. The reaction time varies with the reaction scale and the reaction temperature, but is usually in the range of a few minutes to 48 hours.

After the reaction is completed, the compound of interest is isolated from the post-reaction mixture by the usual method. As needed, recrystallization, column chromatography, etc. can be employed for the purification of the compound of interest.

Step [h]

The compound represented by the general formula (2'-d) can be produced by allowing the compound represented by the general formula (2'-e) to react in the presence of DPPA (diphenylphosphoryl azide) and a tert-butyl alcohol according to the method described in J. A. Chem. Soc. 1972, 94, 6203-6205.

Step [i]

The compound represented by the general formula (2'-c) can be produced by allowing the compound represented by the general formula (2'-d) to react in the presence of an acid and an inert solvent.

Examples of the acid used in this reaction include inorganic acids such as hydrochloric acid, sulfuric acid and nitric acid; organic acids such as formic acid, acetic acid, propionic acid, trifluoroacetic acid and benzoic acid; and sulfonic acids such as methanesulfonic acid and trifluoromethanesulfonic acid. The amount of the acid used is usually selected as appropriate from the range of a 1- to 10-fold molar amount relative to the compound represented by the general formula (2'-d). In some cases, the acid can be used to serve as the solvent as well.

The inert solvent used in this reaction may be any solvent that does not markedly inhibit the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide and 1,3-dimethyl-2-imidazolidinone. One of these inert solvents may be used alone, and also two or more of them may be used as a mixture. The amount of the inert solvent used is usually selected as appropriate from the range of 0.1 to 100 L relative to 1 mol of the compound represented by the general formula (2'-d).

The reaction temperature is usually in the range of –10° C. to the boiling point of the inert solvent used. The reaction time varies with the reaction scale and the reaction temperature, but is usually in the range of a few minutes to 48 hours. After the reaction is completed, the compound of interest is isolated from the post-reaction mixture by the usual method. As needed, recrystallization, column chromatography, etc. can be employed for the purification of the compound of interest.

Step [j]

The compound represented by the general formula (2'-b) can be produced by halogenating the compound represented by the general formula (2'-c) via the Sandmeyer reaction as described in Chem. Rev. 1988, 88, 765, and esterifying the resulting compound in the usual manner of organic synthesis.

Step [k]

The compound represented by the general formula (2'-a) can be produced by cross-coupling the compound represented by the general formula (2'-b) with cyclopropylboronic acid in the presence of a transition metal catalyst, a base and an inert solvent.

The transition metal catalyst used in this reaction may be, for example, $PdCl_2$(dppf) acetone adduct or the like. The amount of the transition metal catalyst used is usually selected as appropriate from the range of 0.01 to 100 mol % relative to the compound represented by the general formula (2'-b).

The base used in this reaction may be, for example, potassium phosphate (tribasic) or the like. The amount of the base used is usually selected as appropriate from the range of a 1- to 10-fold molar amount relative to the compound represented by the general formula (2'-b).

Examples of the inert solvent used in this reaction include ether solvents such as diethyl ether and THF. The amount of the inert solvent used is usually selected as appropriate from the range of 0.1 to 100 L relative to 1 mol of the compound represented by the general formula (2'-b).

Since this reaction is an equimolar reaction of the reactants, the compound represented by the general formula (2'-b) and cyclopropylboronic acid are used basically in equimolar amounts, but either of them may be used in an excess amount. The reaction temperature is usually in the range of room temperature to the boiling point of the inert solvent used. The reaction time varies with the reaction scale and the reaction temperature, but is usually in the range of a few minutes to 48 hours. After the reaction is completed, the compound of interest is isolated from the post-reaction mixture by the usual method. As needed, recrystallization, column chromatography, etc. can be employed for the purification of the compound of interest.

Step [l]

The compound represented by the general formula (2') can be produced by hydrolyzing the ester group of the compound represented by the general formula (2'-a) in the usual manner of organic synthesis.

Specific examples of the compound of the present invention are shown below. In the following tables, shown in the column of "Physical property" is a melting point (° C.).

[Chem. 5]

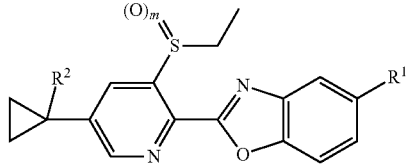

(1)

TABLE 1

| Compound No. | $R^1$ | $R^2$ | m | Physical property value |
|---|---|---|---|---|
| 1-1 | $OCF_3$ | H | 0 | 108-110 |
| 1-2 | $OCF_3$ | H | 1 | |
| 1-3 | $OCF_3$ | H | 2 | 113-114 |
| 1-4 | $OCHF_2$ | H | 0 | 87-89 |
| 1-5 | $OCHF_2$ | H | 1 | 167-169 |
| 1-6 | $OCHF_2$ | H | 2 | 126-128 |
| 1-7 | $OCF_2CHF_2$ | H | 0 | |
| 1-8 | $OCF_2CHF_2$ | H | 1 | |
| 1-9 | $OCF_2CHF_2$ | H | 2 | |
| 1-10 | $SOCF_3$ | H | 0 | |
| 1-11 | $SOCF_3$ | H | 1 | |
| 1-12 | $SOCF_3$ | H | 2 | 58-60 |
| 1-13 | $SO_2CF_3$ | H | 0 | |
| 1-14 | $SO_2CF_3$ | H | 1 | |
| 1-15 | $SO_2CF_3$ | H | 2 | 177-178 |
| 1-16 | $SCHF_2$ | H | 0 | 143-145 |
| 1-17 | $SCHF_2$ | H | 1 | 163-165 |
| 1-18 | $SCHF_2$ | H | 2 | NMR |
| 1-19 | $OCF_2CHF_2$ | H | 0 | |
| 1-20 | $OCF_2CHF_2$ | H | 1 | |

TABLE 2

Table 1 (Continued)

| Compound No. | $R^1$ | $R^2$ | m | Physical property value |
|---|---|---|---|---|
| 1-21 | $OCF_2CHF_2$ | H | 2 | |
| 1-22 | $OCF_3$ | CN | 0 | |
| 1-23 | $OCF_3$ | CN | 1 | |
| 1-24 | $OCF_3$ | CN | 2 | |
| 1-25 | $OCHF_2$ | CN | 0 | |
| 1-26 | $OCHF_2$ | CN | 1 | |
| 1-27 | $OCHF_2$ | CN | 2 | |
| 1-28 | $OCF_2CHF_2$ | CN | 0 | |
| 1-29 | $OCF_2CHF_2$ | CN | 1 | |
| 1-30 | $OCF_2CHF_2$ | CN | 2 | |

TABLE 2-continued

Table 1 (Continued)

| Compound No. | R¹ | R² | m | Physical property value |
|---|---|---|---|---|
| 1-31 | SOCF$_3$ | CN | 0 | |
| 1-32 | SOCF$_3$ | CN | 1 | |
| 1-33 | SOCF$_3$ | CN | 2 | |
| 1-34 | SO$_2$CF$_3$ | CN | 0 | |
| 1-35 | SO$_2$CF$_3$ | CN | 1 | |
| 1-36 | SO$_2$CF$_3$ | CN | 2 | |
| 1-37 | SCHF$_2$ | CN | 0 | |
| 1-38 | SCHF$_2$ | CN | 1 | |
| 1-39 | SCHF$_2$ | CN | 2 | |
| 1-40 | OCF$_2$CHF$_2$ | CN | 0 | |
| 1-41 | OCF$_2$CHF$_2$ | CN | 1 | |
| 1-42 | OCF$_2$CHF$_2$ | CN | 2 | |

The agricultural and horticultural insecticide comprising the benzoxazole compound represented by the general formula (1) of the present invention or a salt thereof as an active ingredient is suitable for controlling a variety of pests which may damage paddy rice, fruit trees, vegetables, other crops and ornamental flowering plants. The target pests are, for example, agricultural and forest pests, horticultural pests, stored grain pests, sanitary pests, nematodes, etc.

Specific examples of the pests, nematodes, etc. include the following:

the species of the order Lepidoptera such as *Parasa consocia, Anomis mesogona, Papilio xuthus, Matsumuraeses azukivora, Ostrinia scapulalis, Spodoptera exempta, Hyphantria cunea, Ostrinia furnacalis, Pseudaletia separata, Tinea translucens, Bactra furfurana, Parnara guttata, Marasmia exigua, Parnara guttata, Sesamia inferens, Brachmia triannulella, Monema flavescens, Trichoplusia ni, Pleuroptya ruralis, Cystidia couaggaria, Lampides boeticus, Cephonodes hylas, Helicoverpa armigera, Phalerodonta manleyi, Eumeta japonica, Pieris brassicae, Malacosoma neustria testacea, Stathmopoda masinissa, Cuphodes diospyrosella, Archips xylosteanus, Agrotis segetum, Tetramoera schistaceana, Papilio machaon hippocrates, Endoclyta sinensis, Lyonetia prunifoliella, Phyllonorycter ringoneella, Cydia kurokoi, Eucoenogenes aestuosa, Lobesia botrana, Latoia sinica, Euzophera batangensis, Phalonidia mesotypa, Spilosoma imparilis, Glyphodes pyloalis, Olethreutes mori, Tineola bisselliella, Endoclyta excrescens, Nemapogon granellus, Synanthedon hector, Cydia pomonella, Plutella xylostella, Cnaphalocrocis medinalis, Sesamia calamistis, Scirpophaga incertulas, Pediasia teterrellus, Phthorimaea operculella, Stauropus fagi persimilis, Etiella zinckenella, Spodoptera exigua, Palpifer sexnotata, Spodoptera mauritia, Scirpophaga innotata, Xestia c-nigrum, Spodoptera depravata, Ephestia kuehniella, Angerona prunaria, Clostera anastomosis, Pseudoplusia includens, Matsumuraeses falcana, Helicoverpa assulta, Autographa nigrisigna, Agrotis Euproctis pseudoconspersa, Adoxophyes orana, Caloptilia theivora, Homona magnanima, Ephestia elutella, Eumeta minuscula, Clostera anachoreta, Heliothis maritima, Sparganothis pilleriana, Busseola fusca, Euproctis subflava, Biston robustum, Heliothis zea, Aedia leucomelas, Narosoideus flavidorsalis, Viminia rumicis, Bucculatrix pyrivorella, Grapholita molesta, Spulerina astaurota, Ectomyelois pyrivorella, Chilo suppressalis, Acrolepiopsis sapporensis, Plodia interpunctella, Hellula undalis, Sitotroga cerealella, Spodoptera litura, a species of the family Tortricidae (Eucosma aporema), Acleris comariana, Scopelodes contractus, Orgyia thyellina, Spodoptera frugiperda, Ostrinia zaguliaevi, Naranga aenescens, Andraca bipunctata, Paranthrene regalis, Acosmeryx castanea, Phyllocnistis toparcha, Endopiza viteana, Eupoecillia ambiguella, Anticarsia gemmatalis, Cnephasia cinereipalpana, Lymantria dispar, Dendrolimus spectabilis, Leguminivora glycinivorella, Maruca testulalis, Matsumuraeses phaseoli, Caloptilia soyella, Phyllocnistis citrella, Omiodes indicata, Archips fuscocupreanus, Acanthoplusia agnata, Bambalina sp., Carposina niponensis, Conogethes punctiferalis, Synanthedon sp., Lyonetia clerkella, Papilio helenus, Colias erate poliographus, Phalera flavescens*, the species of the family Pieridae such as *Pieris rapae crucivora* and *Pieris rapae, Euproctis similis, Acrolepiopsis suzukiella, Ostrinia nubilalis, Namestra brassicae, Ascotis selenaria, Phtheochroides clandestina, Hoshinoa adumbratana, Odonestis pruni japonensis, Triaena intermedia, Adoxophyes orana fasciata, Grapholita inopinata, Spilonota ocellana, Spilonota lechriaspis, Illiberis pruni, Argyresthia conjugella, Caloptilia zachrysa, Archips breviplicanus, Anomis flava, Pectinophora gossypiella, Notarcha derogata, Diaphania indica, Heliothis virescens* and *Earias cupreoviridis*;

the species of the order Hemiptera such as *Nezara antennata, Stenotus rubrovittatus, Graphosoma rubrolineatum, Trigonotylus coelestialium, Aeschynteles maculatus, Creontiades pallidifer, Dysdercus cingulatus, Chrysomphalus ficus, Aonidiella aurantii, Graptopsaltria nigrofuscata, Blissus leucopterus, Icerya purchasi, Piezodorus hybneri, Lagynotomus elongatus, Thaia subrufa, Scotinophara lurida, Sitobion ibarae, Stariodes iwasakii, Aspidiotus destructor, Taylorilygus pallidulus, Myzus mumecola, Pseudaulacaspis prunicola, Acyrthosiphon pisum, Anacanthocoris striicornis, Ectometopterus micantulus, Eysarcoris lewisi, Molipteryx fuliginosa, Cicadella viridis, Rhopalosiphum rufiabdominalis, Saissetia oleae, Trialeurodes vaporariorum, Aguriahana quercus, Lygus* spp., *Euceraphis punctipennis, Andaspis kashicola, Coccus pseudomagnoliarum, Cavelerius saccharivorus, Galeatus spinifrons, Macrosiphoniella sanborni, Aonidiella citrina, Halyomorpha mista, Stephanitis fasciicarina, Trioza camphorae, Leptocorisa chinensis, Trioza quercicola, Uhlerites latius, Erythroneura comes, Paromius exiguus, Duplaspidiotus claviger, Nephotettix nigropictus, Halticiellus insularis, Perkinsiella saccharicida, Psylla malivorella, Anomomeura mori, Pseudococcus longispinis, Pseudaulacaspis pentagona, Pulvinaria kuwacola, Apolygus lucorum, Togo hemipterus, Toxoptera aurantii, Saccharicoccus sacchari, Geoica lucifuga, Numata muiri, Comstockaspis perniciosa, Unaspis citri, Aulacorthum solani, Eysarcoris ventralis, Bemisia argentifolii, Cicadella spectra, Aspidiotus hederae, Liorhyssus hyalinus, Calophya nigridorsalis, Sogatella furcifera, Megoura crassicauda, Brevicoryne brassicae, Aphis glycines, Leptocorisa oratorius, Nephotettix virescens, Uroeucon formosanum, Cyrtopeltis tennuis, Bemisia tabaci, Lecanium persicae, Parlatoria theae, Pseudaonidia paeoniae, Empoasca onukii, Plautia stali, Dysaphis tulipae, Macrosiphum euphorbiae, Stephanitis pyrioides, Ceroplastes ceriferus, Parlatoria camelliae, Apolygus spinolai, Nephotettix cincticeps, Glaucias subpunctatus, Orthotylus flavosparsus, Rhopalosiphum maidis, Peregrinus maidis, Eysarcoris parvus, Cimex lectularius, Psylla abieti, Nilaparvata lugens, Psylla tobirae, Eurydema rugosum, Schizaphis piricola, Psylla pyricola, Parlatoreopsis pyri, Stephanitis nashi, Dysmicoccus wistariae, Lepholeucaspis japonica, Sappaphis piri, Lipaphis erysimi, Neotoxoptera formosana, Rhopalosiphum nymphaeae, Edwardsiana rosae, Pinnaspis aspidistrae, Psylla alni, Speusotettix subfusculus, Alnetoidia alneti, Sogatella panicicola, Adelphocoris lineolatus, Dysdercus poecilus, Parla-* toria ziziphi, Uhlerites debile, Laodelphax striatellus, Eurydema pulchrum, Cletus trigonus, Clovia punctata, Empoasca spp., Coccus hesperidum, Pachybrachius luridus, Planococcus kraunhiae, Stenotus binotatus, Arboridia apicalis, Macrosteles fascifrons, Dolycoris baccarum, Adelphocoris triannulatus, Viteus vitifolii, Acanthocoris sordidus, Leptocorisa acuta, Macropes obnubilus, Cletus punctiger, Riptortus clavatus, Paratrioza cockerelli, Aphrophora costalis, Lygus disponsi, Lygus saundersi, Crisicoccus pini, Empoasca abietis, Crisicoccus matsumotoi, Aphis craccivora, Megacopta punctatissimum, Eysarcoris guttiger, Lepidosaphes beckii, Diaphorina citri, Toxoptera citricidus, Planococcus citri, Dialeurodes citri, Aleurocanthus spiniferus, Pseudococcus citriculus, Zyginella citri, Pulvinaria citricola, Coccus discrepans, Pseudaonidia duplex, Pulvinaria aurantii, Lecanium corni, Nezara viridula, Stenodema calcaratum, Rhopalosiphum padi, Sitobion akebiae, Schizaphis graminum, Sorhoanus tritici, Brachycaudus helichrysi, Carpocoris purpureipennis, Myzus persicae, Hyalopterus pruni, Aphis farinose yanagicola, Metasalis populi, Unaspis yanonensis, Mesohomotoma camphorae, Aphis spiraecola, Aphis pomi, Lepidosaphes ulmi, Psylla mali, Heterocordylus flavipes, Myzus malisuctus, Aphidonuguis mali, Orientus ishidai, Ovatus malicolens, Eriosoma lanigerum, Ceroplastes rubens and Aphis gossypii;

the species of the order Coleoptera such as *Xystrocera globosa, Paederus fuscipes, Eucetonia roelofsi, Callosobruchus chinensis, Cylas formicarius, Hypera postica, Echinocnemus squameus, Oulema oryzae, Donacia provosti, Lissorhoptrus oryzophilus, Colasposoma dauricum, Euscepes postfasciatus, Epilachna varivestis, Acanthoscelides obtectus, Diabrotica virgifera virgifera, Involvulus cupreus, Aulacophora femoralis, Bruchus pisorum, Epilachna vigintioctomaculata, Carpophilus dimidiatus, Cassida nebulosa, Luperomorpha tunebrosa, Phyllotreta striolata, Psacothea hilaris, Aeolesthes chrysothrix, Curculio sikkimensis, Carpophilus hemipterus, Oxycetonia jucunda, Diabrotica* spp., *Mimela splendens, Sitophilus zeamais, Tribolium castaneum, Sitophilus oryzae, Palorus subdepressus, Melolontha japonica, Anoplophora malasiaca, Neatus picipes, Leptinotarsa decemlineata, Diabrotica undecimpunctata howardi, Sphenophorus venatus, Crioceris quatuordecimpunctata, Conotrachelus nenuphar, Ceuthorhynchidius albosuturalis, Phaedon brassicae, Lasioderma serricorne, Sitona japonicus, Adoretus tenuimaculatus, Tenebrio molitor, Basilepta balyi, Hypera nigrirostris, Chaetocnema concinna, Anomala cuprea, Heptophylla picea, Epilachna vigintioctopunctata, Diabrotica longicornis, Eucetonia pilifera, Agriotes* spp., *Attagenus unicolor japonicus, Pagria signata, Anomala rufocuprea, Palorus ratzeburgii, Alphitobius laevigatus, Anthrenus verbasci, Lyctus brunneus, Tribolium confusum, Medythia nigrobilineata, Xylotrechus pyrrhoderus, Epitrix cucumeris, Tomicus piniperda, Monochamus alternatus, Popillia japonica, Epicauta gorhami, Sitophilus zeamais, Rhynchites heros, Listroderes costirostris, Callosobruchus maculatus, Phyllobius armatus, Anthonomus pomorum, Linaeidea aenea* and *Anthonomus grandis;* the species of the order Diptera such as *Culex pipiens pallens, Pegomya hyoscyami, Liriomyza huidobrensis, Musca domestica, Chlorops oryzae, Hydrellia sasakii, Agromyza oryzae, Hydrellia griseola, Hydrellia griseola, Ophiomyia phaseoli, Dacus cucurbitae, Drosophila suzukii, Rhacochlaena japonica, Muscina stabulans,* the species of the family Phoridae such as *Megaselia spiracularis, Clogmia albipunctata, Tipula aino, Phormia regina, Culex tritaeniorhynchus, Anopheles sinensis, Hylemya brassicae, Asphondylia* sp., *Delia platura, Delia antiqua, Rhagoletis cerasi, Culex pipiens molestus Forskal, Ceratitis capitata, Bradysia agrestis, Pegomya cunicularia, Liriomyza sativae, Liriomyza bryoniae, Chromatomyia horticola, Liriomyza chinensis, Culex quinquefasciatus, Aedes aegypti, Aedes albopictus, Liriomyza trifolii, Liriomyza sativae, Dacus dorsalis, Dacus tsuneonis, Sitodiplosis mosellana, Meromuza nigriventris, Anastrepha ludens* and *Rhagoletis pomonella;* the species of the order Hymenoptera such as *Pristomyrmex pungens*, the species of the family Bethylidae, *Monomorium pharaonis, Pheidole noda, Athalia rosae, Dryocosmus kuriphilus, Formica fusca japonica*, the species of the subfamily Vespinae, *Athalia infumata infumata, Arge pagana, Athalia japonica, Acromyrmex* spp., *Solenopsis* spp., *Arge mali* and *Ochetellus glaber;* the species of the order Orthoptera such as *Homorocoryphus lineosus, Gryllotalpa* sp., *Oxya hyla intricata, Oxya yezoensis, Locusta migratoria, Oxya japonica, Homorocoryphus jezoensis* and *Teleogryllus emma;* the species of the order Thysanoptera such as *Selenothrips rubrocinctus, Stenchaetothrips biformis, Haplothrips aculeatus, Ponticulothrips diospyrosi, Thrips flavus, Anaphothrips obscurus, Liothrips floridensis, Thrips simplex, Thrips nigropilosus, Heliothrips haemorrhoidalis, Pseudodendrothrips mori, Microcephalothrips abdominalis, Leeuwenia pasanii, Litotetothrips pasaniae, Scirtothrips citri, Haplothrips chinensis, Mycterothrips glycines, Thrips setosus, Scirtothrips dorsalis, Dendrothrips minowai, Haplothrips niger, Thrips tabaci, Thrips alliorum, Thrips hawaiiensis, Haplothrips kurdjumovi, Chirothrips manicatus, Frankliniella intonsa, Thrips coloratus, Franklinella occidentalis, Thrips palmi, Frankliniella lilivora* and *Liothrips vaneeckei;* the species of the order Acari such as *Leptotrombidium akamushi, Tetranychus ludeni, Dermacentor variabilis, Tetranychus truncatus, Ornithonyssus bacoti, Demodex canis, Tetranychus viennensis, Tetranychus kanzawai*, the species of the family Ixodidae such as *Rhipicephalus sanguineus, Cheyletus malaccensis, Tyrophagus putrescentiae, Dermatophagoides farinae, Latrodectus hasseltii, Dermacentor taiwanicus, Acaphylla theavagrans, Polyphagotarsonemus latus, Aculops lycopersici, Ornithonyssus sylvairum, Tetranychus urticae, Eriophyes chibaensis, Sarcoptes scabiei, Haemaphysalis longicornis, Ixodes scapularis, Tyrophagus similis, Cheyletus eruditus, Panonychus citri, Cheyletus moorei, Brevipalpus phoenicis, Octodectes cynotis, Dermatophagoides ptrenyssnus, Haemaphysalis flava, Ixodes ovatus, Phyllocoptruta citri, Aculus schlechtendali, Panonychus ulmi, Amblyomma americanum, Dermanyssus gallinae, Rhyzoglyphus robini* and *Sancassania* sp.;

the species of the order Isoptera such as *Reticulitermes miyatakei, Incisitermes minor, Coptotermes formosanus, Hodotermopsis japonica, Reticulitermes* sp., *Reticulitermes flaviceps amamianus, Glyptotermes kushimensis, Coptotermes guangzhoensis, Neotermes koshunensis, Glyptotermes kodamai, Glyptotermes satsumensis, Cryptotermes domesticus, Odontotermes formosanus, Glyptotermes nakajimai, Pericapritermes nitobei* and *Reticulitermes speratus;* the species of the order Blattodea such as *Periplaneta fuliginosa, Blattella germanica, Blatta orientalis, Periplaneta brunnea, Blattella lituricollis, Periplaneta japonica* and *Periplaneta americana;* the species of the order Siphonaptera such as *Pulex irritans, Ctenocephalides felis* and *Ceratophyllus gallinae;* the species of the phylum Nematoda such as *Nothotylenchus acris, Aphelenchoides besseyi, Pratylenchus penetrans, Meloidogyne hapla, Meloidogyne incognita, Globodera*

*rostochiensis, Meloidogyne javanica, Heterodera glycines, Pratylenchus coffeae, Pratylenchus neglectus* and *Tylenchus semipenetrans*; and the species of the phylum Mollusca such as *Pomacea canaliculata, Achatina fulica, Meghimatium bilineatum, Lehmannina valentiana, Limax flavus* and *Acusta despecta sieboldiana*.

In addition, the agricultural and horticultural insecticide of the present invention has a strong insecticidal effect on *Tuta absoluta* as well.

Further, mites and ticks parasitic on animals are also included in the target pests, and the examples include the species of the family Ixodidae such as *Boophilus microplus, Rhipicephalus sanguineus, Haemaphysalis longicornis, Haemaphysalis flava, Haemaphysalis campanulata, Haemaphysalis concinna, Haemaphysalis japonica, Haemaphysalis kitaokai, Haemaphysalis ias, Ixodes ovatus, Ixodes nipponensis, Ixodes persulcatus, Amblyomma testudinarium, Haemaphysalis megaspinosa, Dermacentor reticulatus* and *Dermacentor taiwanesis; Dermanyssus gallinae*; the species of the genus *Ornithonyssus* such as *Ornithonyssus sylviarum* and *Ornithonyssus bursa*; the species of the family Trombiculidae such as *Eutrombicula wichmanni, Leptotrombidium akamushi, Leptotrombidium pallidum, Leptotrombidium fuji, Leptotrombidium tosa, Neotrombicula autumnalis, Eutrombicula alfreddugesi* and *Helenicula miyagawai*; the species of the family Cheyletidae such as *Cheyletiella yasguri, Cheyletiella parasitivorax* and *Cheyletiella blakei*; the species of the superfamily Sarcoptoidea such as *Psoroptes cuniculi, Chorioptes bovis, Otodectes cynotis, Sarcoptes scabiei* and *Notoedres cati*; and the species of the family Demodicidae such as *Demodex canis*.

Other target pests include fleas including ectoparasitic wingless insects belonging to the order Siphonaptera, more specifically, the species belonging to the families Pulicidae and Ceratophyllidae. Examples of the species belonging to the family Pulicidae include *Ctenocephalides canis, Ctenocephalides felis, Pulex irritans, Echidnophaga gallinacea, Xenopsylla cheopis, Leptopsylla segnis, Nosopsyllus fasciatus* and *Nosopsyllus anisus*.

Other target pests include ectoparasites, for example, the species of the suborder Anoplura such as *Haematopinus eurysternus, Haematopinus asini, Dalmalinia ovis, Linognathus vituli, Haematopinus suis, Phthirus pubis* and *Pediculus capitis*; the species of the suborder Mallophaga such as *Trichodectes canis*; and hematophagous Dipteran insect pests such as *Tabanus trigonus, Culicoides schultzei* and *Simulium ornatum*. In addition, examples of endoparasites include nematodes such as lungworms, whipworms, nodular worms, endogastric parasitic worms, ascarides and filarial worms; cestodes such as *Spirometra erinacei, Diphyllobothrium latum, Dipylidium caninum, Multiceps multiceps, Echinococcus granulosus* and *Echinococcus multilocularis*; trematodes such as *Schistosoma japonicum* and *Fasciola hepatica*; and protozoa such as coccidia, *Plasmodium*, intestinal *Sarcocystis, Toxoplasma* and *Cryptosporidium*.

The benzoxazole compound represented by the general formula (1) of the present invention or a salt thereof may be internally or externally administered.

The agricultural and horticultural insecticide comprising the benzoxazole compound represented by the general formula (1) of the present invention or a salt thereof as an active ingredient has a remarkable control effect on the above-described pests which damage lowland crops, field crops, fruit trees, vegetables, other crops, ornamental flowering plants, etc. The desired effect can be obtained when the agricultural and horticultural insecticide is applied to nursery facilities for seedlings, paddy fields, fields, fruit trees, vegetables, other crops, ornamental flowering plants, etc. and their seeds, paddy water, foliage, cultivation media such as soil, or the like around the expected time of pest infestation, i.e., before the infestation or upon the confirmation of the infestation. In particularly preferable embodiments, the application of the agricultural and horticultural insecticide utilizes so-called penetration and translocation. That is, nursery soil, soil in transplanting holes, plant foot, irrigation water, cultivation water in hydroponics, or the like is treated with the agricultural and horticultural insecticide to allow crops, ornamental flowering plants, etc. to absorb the compound of the present invention through the roots via soil or otherwise.

Examples of useful plants to which the agricultural and horticultural insecticide of the present invention can be applied include, but are not particularly limited to, cereals (e.g., rice, barley, wheat, rye, oats, corn, etc.), legumes (e.g., soybeans, azuki beans, broad beans, green peas, kidney beans, peanuts, etc.), fruit trees and fruits (e.g., apples, citrus fruits, pears, grapes, peaches, plums, cherries, walnuts, chestnuts, almonds, bananas, etc.), leaf and fruit vegetables (e.g., cabbages, tomatoes, spinach, broccoli, lettuce, onions, green onions (chives and Welsh onions), green peppers, eggplants, strawberries, pepper crops, okra, Chinese chives, etc.), root vegetables (e.g., carrots, potatoes, sweet potatoes, taros, Japanese radishes, turnips, lotus roots, burdock roots, garlic, Chinese scallions, etc.), crops for processing (e.g., cotton, hemp, beet, hops, sugarcane, sugar beet, olives, rubber, coffee, tobacco, tea, etc.), gourds (e.g., Japanese pumpkins, cucumbers, watermelons, oriental sweet melons, melons, etc.), pasture grass (e.g., orchardgrass, sorghum, timothy, clover, alfalfa, etc.), lawn grass (e.g., Korean lawn grass, bent grass, etc.), spice and aromatic crops and ornamental crops (e.g., lavender, rosemary, thyme, parsley, pepper, ginger, etc.), ornamental flowering plants (e.g., *chrysanthemum*, rose, carnation, orchid, tulip, lily, etc.), garden trees (e.g., ginkgo trees, cherry trees, Japanese *aucuba*, etc.) and forest trees (e.g., *Abies sachalinensis, Picea jezoensis*, pine, yellow cedar, Japanese cedar, hinoki cypress, *eucalyptus*, etc.).

The above-mentioned "plants" also include plants provided with herbicide tolerance by a classical breeding technique or a gene recombination technique. Examples of such herbicide tolerance include tolerance to HPPD inhibitors, such as isoxaflutole; ALS inhibitors, such as imazethapyr and thifensulfuron-methyl; EPSP synthase inhibitors, such as glyphosate; glutamine synthetase inhibitors, such as glufosinate; acetyl-CoA carboxylase inhibitors, such as sethoxydim; or other herbicides, such as bromoxynil, dicamba and 2,4-D.

Examples of the plants provided with herbicide tolerance by a classical breeding technique include varieties of rapeseed, wheat, sunflower and rice tolerant to the imidazolinone family of ALS-inhibiting herbicides such as imazethapyr, and such plants are sold under the trade name of Clearfield (registered trademark). Also included is a variety of soybean provided with tolerance to the sulfonyl urea family of ALS-inhibiting herbicides such as thifensulfuron-methyl by a classical breeding technique, and this is sold under the trade name of STS soybean. Also included are plants provided with tolerance to acetyl-CoA carboxylase inhibitors such as trione oxime herbicides and aryloxy phenoxy propionic acid herbicides by a classical breeding technique, for example, SR corn and the like.

Plants provided with tolerance to acetyl-CoA carboxylase inhibitors are described in Proc. Natl. Acad. Sci. USA, 87, 7175-7179 (1990), and the like. Further, acetyl-CoA carboxylase mutants resistant to acetyl-CoA carboxylase inhibitors are reported in Weed Science, 53, 728-746 (2005), and the like, and by introducing the gene of such an acetyl-CoA carboxylase mutant into plants by a gene recombination technique, or introducing a resistance-conferring mutation into acetyl-CoA carboxylase of plants, plants tolerant to acetyl-CoA carboxylase inhibitors can be engineered. Alternatively, by introducing a nucleic acid causing base substitution mutation into plant cells (a typical example of this technique is chimeraplasty technique (Gura T. 1999. Repairing the Genome's Spelling Mistakes. Science 285: 316-318.)) to allow site-specific substitution mutation in the amino acids encoded by an acetyl-CoA carboxylase gene, an ALS gene or the like of plants, plants tolerant to acetyl-CoA carboxylase inhibitors, ALS inhibitors or the like can be engineered. The agricultural and horticultural insecticide of the present invention can be applied to these plants as well.

Further, exemplary toxins expressed in genetically modified plants include insecticidal proteins of *Bacillus cereus* or *Bacillus popilliae*; *Bacillus thuringiensis* δ-endotoxins, such as Cry1Ab, Cry1Ac, Cry1F, Cry1Fa2, Cry2Ab, Cry3A, Cry3Bb1 and Cry9C, and other insecticidal proteins, such as VIP1, VIP2, VIP3 and VIP3A; nematode insecticidal proteins; toxins produced by animals, such as scorpion toxins, spider toxins, bee toxins and insect-specific neurotoxins; toxins of filamentous fungi; plant lectins; agglutinin; protease inhibitors, such as trypsin inhibitors, serine protease inhibitors, patatin, cystatin and papain inhibitors; ribosome inactivating proteins (RIP), such as ricin, maize RIP, abrin, luffin, saporin and bryodin; steroid metabolizing enzymes, such as 3-hydroxy steroid oxidase, ecdysteroid-UDP-glucosyltransferase and cholesterol oxidase; ecdysone inhibitors; HMG-CoA reductase; ion channel inhibitors, such as sodium channel inhibitors and calcium channel inhibitors; juvenile hormone esterase; diuretic hormone receptors; stilbene synthase; bibenzyl synthase; chitinase; and glucanase.

Also included are hybrid toxins, partially deficient toxins and modified toxins derived from the following: δ-endotoxin proteins such as Cry1Ab, Cry1Ac, Cry1F, Cry1Fa2, Cry2Ab, Cry3A, Cry3Bb1, Cry9C, Cry34Ab and Cry35Ab, and other insecticidal proteins such as VIP1, VIP2, VIP3 and VIP3A. The hybrid toxin can be produced by combining some domains of these proteins differently from the original combination in nature with the use of a recombination technique. As the partially deficient toxin, a Cry1Ab toxin in which a part of the amino acid sequence is deleted is known. In the modified toxin, one or more amino acids of a naturally occurring toxin are substituted.

Examples of the foregoing toxins and genetically modified plants capable of synthesizing these toxins are described in EP-A-0 374 753, WO 93/07278, WO 95/34656, EP-A-0 427 529, EP-A-451 878, WO 03/052073, etc.

Due to the toxins contained in such genetically modified plants, the plants exhibit resistance to pests, in particular, Coleopteran insect pests, Hemipteran insect pests, Dipteran insect pests, Lepidopteran insect pests and nematodes. The above-described technologies and the agricultural and horticultural insecticide of the present invention can be used in combination or used systematically.

In order to control target pests, the agricultural and horticultural insecticide of the present invention, with or without appropriate dilution or suspension in water etc., is applied to plants potentially infested with the target insect pests or nematodes in an amount effective for the control of the insect pests or nematodes. For example, in order to control insect pests and nematodes that may damage crop plants such as fruit trees, cereals and vegetables, foliar application and seed treatment such as dipping, dust coating and calcium peroxide coating can be performed. Further, treatment of soil or the like may also be performed to allow plants to absorb agrochemicals through their roots. Examples of such treatment include whole soil incorporation, planting row treatment, bed soil incorporation, plug seedling treatment, planting hole treatment, plant foot treatment, top-dressing, treatment of nursery boxes for paddy rice, and submerged application. In addition, application to culture media in hydroponics, smoking treatment, trunk injection and the like can also be performed.

Further, the agricultural and horticultural insecticide of the present invention, with or without appropriate dilution or suspension in water etc., can be applied to sites potentially infested with pests in an amount effective for the control of the pests. For example, it can be directly applied to stored grain pests, house pests, sanitary pests, forest pests, etc., and also be used for coating of residential building materials, for smoking treatment, or as a bait formulation.

Exemplary methods of seed treatment include dipping of seeds in a diluted or undiluted fluid of a liquid or solid formulation for the permeation of agrochemicals into the seeds; mixing or dust coating of seeds with a solid or liquid formulation for the adherence of the formulation onto the surfaces of the seeds; coating of seeds with a mixture of a solid or liquid formulation and an adhesive carrier such as resins and polymers; and application of a solid or liquid formulation to the vicinity of seeds at the same time as seeding.

The term "seed" in the above-mentioned seed treatment refers to a plant body which is in the early stages of cultivation and used for plant propagation. The examples include, in addition to a so-called seed, a plant body for vegetative propagation, such as a bulb, a tuber, a seed potato, a bulbil, a propagule, a discoid stem and a stem used for cuttage.

The term "soil" or "cultivation medium" in the method of the present invention for using an agricultural and horticultural insecticide refers to a support medium for crop cultivation, in particular a support medium which allows crop plants to spread their roots therein, and the materials are not particularly limited as long as they allow plants to grow. Examples of the support medium include what is called soils, seedling mats and water, and specific examples of the materials include sand, pumice, vermiculite, diatomite, agar, gelatinous substances, high-molecular-weight substances, rock wool, glass wool, wood chip and bark.

Exemplary methods of the application to crop foliage or to stored grain pests, house pests, sanitary pests, forest pests, etc. include application of a liquid formulation, such as an emulsifiable concentrate and a flowable, or a solid formulation, such as a wettable powder and a water-dispersible granule, after appropriate dilution in water; dust application; and smoking.

Exemplary methods of soil application include application of a water-diluted or undiluted liquid formulation to the foot of plants, nursery beds for seedlings, or the like; application of a granule to the foot of plants, nursery beds for seedlings, or the like; application of a dust, a wettable powder, a water-dispersible granule, a granule or the like onto soil and subsequent incorporation of the formulation into the whole soil before seeding or transplanting; and application of a dust, a wettable powder, a water-dispersible granule, a granule or the like to planting holes, planting rows or the like before seeding or planting.

To nursery boxes for paddy rice, for example, a dust, a water-dispersible granule, a granule or the like can be applied, although the suitable formulation may vary depending on the application timing, in other words, depending on the cultivation stage such as seeding time, greening period and planting time. A formulation such as a dust, a water-dispersible granule and a granule may be mixed with nursery soil. For example, such a formulation is incorporated into bed soil, covering soil or the whole soil. Simply, nursery soil and such a formulation may be alternately layered.

In the application to paddy fields, a solid formulation, such as a jumbo, a pack, a granule and a water-dispersible granule, or a liquid formulation, such as a flowable and an emulsifiable concentrate, is applied usually to flooded paddy fields. In a rice planting period, a suitable formulation, as it is or after mixed with a fertilizer, may be applied onto soil or injected into soil. In addition, an emulsifiable concentrate, a flowable or the like may be applied to the source of water supply for paddy fields, such as a water inlet and an irrigation device. In this case, treatment can be accomplished with the supply of water and thus achieved in a labor-saving manner.

In the case of field crops, their seeds, cultivation media in the vicinity of their plants, or the like may be treated in the period of seeding to seedling culture. In the case of plants of which the seeds are directly sown in the field, in addition to direct seed treatment, plant foot treatment during cultivation is preferable. Specifically, the treatment can be performed by, for example, applying a granule onto soil, or drenching soil with a formulation in a water-diluted or undiluted liquid form. Another preferable treatment is incorporation of a granule into cultivation media before seeding.

In the case of culture plants to be transplanted, preferable examples of the treatment in the period of seeding to seedling culture include, in addition to direct seed treatment, drench treatment of nursery beds for seedlings with a formulation in a liquid form; and granule application to nursery beds for seedlings. Also included are treatment of planting holes with a granule; and incorporation of a granule into cultivation media in the vicinity of planting points at the time of fix planting.

The agricultural and horticultural insecticide of the present invention is commonly used as a formulation convenient for application, which is prepared in the usual method for preparing agrochemical formulations.

That is, the benzoxazole compound represented by the general formula (1) of the present invention or a salt thereof and an appropriate inactive carrier, and if needed an adjuvant, are blended in an appropriate ratio, and through the step of dissolution, separation, suspension, mixing, impregnation, adsorption and/or adhesion, are formulated into an appropriate form for application, such as a suspension concentrate, an emulsifiable concentrate, a soluble concentrate, a wettable powder, a water-dispersible granule, a granule, a dust, a tablet and a pack.

The composition (agricultural and horticultural insecticide or animal parasite control agent) of the present invention can optionally contain an additive usually used for agrochemical formulations or animal parasite control agents in addition to the active ingredient. Examples of the additive include carriers such as solid or liquid carriers, surfactants, dispersants, wetting agents, binders, tackifiers, thickeners, colorants, spreaders, sticking/spreading agents, antifreezing agents, anti-caking agents, disintegrants and stabilizing agents. If needed, preservatives, plant fragments, etc. may also be used as the additive. One of these additives may be used alone, and also two or more of them may be used in combination.

Examples of the solid carriers include natural minerals, such as quartz, clay, kaolinite, pyrophyllite, sericite, talc, bentonite, acid clay, attapulgite, zeolite and diatomite; inorganic salts, such as calcium carbonate, ammonium sulfate, sodium sulfate and potassium chloride; organic solid carriers, such as synthetic silicic acid, synthetic silicates, starch, cellulose and plant powders (for example, sawdust, coconut shell, corn cob, tobacco stalk, etc.); plastics carriers, such as polyethylene, polypropylene and polyvinylidene chloride; urea; hollow inorganic materials; hollow plastic materials; and fumed silica (white carbon). One of these solid carriers may be used alone, and also two or more of them may be used in combination.

Examples of the liquid carriers include alcohols including monohydric alcohols, such as methanol, ethanol, propanol, isopropanol and butanol, and polyhydric alcohols, such as ethylene glycol, diethylene glycol, propylene glycol, hexylene glycol, polyethylene glycol, polypropylene glycol and glycerin; polyol compounds, such as propylene glycol ether; ketones, such as acetone, methyl ethyl ketone, methyl isobutyl ketone, diisobutyl ketone and cyclohexanone; ethers, such as ethyl ether, dioxane, ethylene glycol monoethyl ether, dipropyl ether and tetrahydrofuran; aliphatic hydrocarbons, such as normal paraffin, naphthene, isoparaffin, kerosene and mineral oil; aromatic hydrocarbons, such as benzene, toluene, xylene, solvent naphtha and alkyl naphthalene; halogenated hydrocarbons, such as dichloromethane, chloroform and carbon tetrachloride; esters, such as ethyl acetate, diisopropyl phthalate, dibutyl phthalate, dioctyl phthalate and dimethyl adipate; lactones, such as γ-butyrolactone; amides, such as dimethylformamide, diethylformamide, dimethylacetamide and N-alkyl pyrrolidinone; nitriles, such as acetonitrile; sulfur compounds, such as dimethyl sulfoxide; vegetable oils, such as soybean oil, rapeseed oil, cotton seed oil and castor oil; and water. One of these liquid carriers may be used alone, and also two or more of them may be used in combination.

Exemplary surfactants used as the dispersant or the wetting/spreading agent include nonionic surfactants, such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkyl aryl ether, polyoxyethylene alkyl phenyl ether, polyoxyethylene dialkyl phenyl ether, polyoxyethylene alkyl phenyl ether-formaldehyde condensates, polyoxyethylene-polyoxypropylene block copolymers, polystyrene-polyoxyethylene block polymers, alkyl polyoxyethylene-polypropylene block copolymer ether, polyoxyethylene alkylamine, polyoxyethylene fatty acid amide, polyoxyethylene fatty acid bis(phenyl ether), polyalkylene benzyl phenyl ether, polyoxyalkylene styryl phenyl ether, acetylene diol, polyoxyalkylene-added acetylene diol, polyoxyethylene ether-type silicone, ester-type silicone, fluorosurfactants, polyoxyethylene castor oil and polyoxyethylene hydrogenated castor oil; anionic surfactants, such as alkyl sulfates, polyoxyethylene alkyl ether sulfates, polyoxyethylene alkyl phenyl ether sulfates, polyoxyethylene styryl phenyl ether sulfates, alkylbenzene sulfonates, alkylaryl sulfonates, lignosulfonates, alkyl sulfosuccinates, naphthalene sulfonates, alkylnaphthalene sulfonates, salts of naphthalenesulfonic acid-formaldehyde condensates, salts of alkylnaphthalenesulfonic acid-formaldehyde condensates, fatty acid salts, polycarboxylic acid salts, polyacrylates, N-methyl-fatty acid sarcosinates, resinates, polyoxyethylene alkyl ether phosphates and polyoxyethylene alkyl phenyl ether phosphates; cationic surfactants including alkyl amine salts, such as lauryl amine hydrochloride, stearyl amine hydrochloride, oleyl amine hydrochloride, stearyl amine acetate, stearyl aminopropyl amine acetate, alkyl trimethyl ammonium chloride and alkyl dimethyl benzalkonium chloride; and amphoteric surfactants, such as amino acid-type or betaine-type amphoteric surfactants. One of these surfactants may be used alone, and also two or more of them may be used in combination.

Examples of the binders or the tackifiers include carboxymethyl cellulose or salts thereof, dextrin, soluble starch, xanthan gum, guar gum, sucrose, polyvinyl pyrrolidone, gum arabic, polyvinyl alcohol, polyvinyl acetate, sodium polyacrylate, polyethylene glycols with an average molecular weight of 6,000 to 20,000, polyethylene oxides with an average molecular weight of 100,000 to 5,000,000, phospholipids (for example, cephalin, lecithin, etc.), cellulose powder, dextrin, modified starch, polyaminocarboxylic acid chelating compounds, cross-linked polyvinyl pyrrolidone, maleic acid-styrene copolymers, (meth)acrylic acid copolymers, half esters of polyhydric alcohol polymer and dicarboxylic anhydride, water soluble polystyrene sulfonates, paraffin, terpene, polyamide resins, polyacrylates, polyoxyethylene, waxes, polyvinyl alkyl ether, alkylphenol-formaldehyde condensates and synthetic resin emulsions.

Examples of the thickeners include water soluble polymers, such as xanthan gum, guar gum, diutan gum, carboxymethyl cellulose, polyvinyl pyrrolidone, carboxyvinyl polymers, acrylic polymers, starch compounds and polysaccharides; and inorganic fine powders, such as high grade bentonite and fumed silica (white carbon).

Examples of the colorants include inorganic pigments, such as iron oxide, titanium oxide and Prussian blue; and organic dyes, such as alizarin dyes, azo dyes and metal phthalocyanine dyes.

Examples of the antifreezing agents include polyhydric alcohols, such as ethylene glycol, diethylene glycol, propylene glycol and glycerin.

Examples of the adjuvants serving to prevent caking or facilitate disintegration include polysaccharides (starch, alginic acid, mannose, galactose, etc.), polyvinyl pyrrolidone, fumed silica (white carbon), ester gum, petroleum resin, sodium tripolyphosphate, sodium hexametaphosphate, metal stearates, cellulose powder, dextrin, methacrylate copolymers, polyvinyl pyrrolidone, polyaminocarboxylic acid chelating compounds, sulfonated styrene-isobutylene-maleic anhydride copolymers and starch-polyacrylonitrile graft copolymers.

Examples of the stabilizing agents include desiccants, such as zeolite, quicklime and magnesium oxide; antioxidants, such as phenolic compounds, amine compounds, sulfur compounds and phosphoric acid compounds; and ultraviolet absorbers, such as salicylic acid compounds and benzophenone compounds.

Examples of the preservatives include potassium sorbate and 1,2-benzothiazolin-3-one.

Further, other adjuvants including functional spreading agents, activity enhancers such as metabolic inhibitors (piperonyl butoxide etc.), antifreezing agents (propylene glycol etc.), antioxidants (BHT etc.) and ultraviolet absorbers can also be used if needed.

The amount of the active ingredient compound in the agricultural and horticultural insecticide of the present invention can be adjusted as needed, and basically, the amount of the active ingredient compound is appropriately selected from the range of 0.01 to 90 parts by weight in 100 parts by weight of the agricultural and horticultural insecticide. For example, in the case where the agricultural and horticultural insecticide is a dust, a granule, an emulsifiable concentrate or a wettable powder, it is suitable that the amount of the active ingredient compound is 0.01 to 50 parts by weight (0.01 to 50% by weight relative to the total weight of the agricultural and horticultural insecticide).

The application rate of the agricultural and horticultural insecticide of the present invention may vary with various factors, for example, the purpose, the target pest, the growing conditions of crops, the tendency of pest infestation, the weather, the environmental conditions, the dosage form, the application method, the application site, the application timing, etc., but basically, the application rate of the active ingredient compound is appropriately selected from the range of 0.001 g to 10 kg, and preferably 0.01 g to 1 kg per 10 ares depending on the purpose.

Furthermore, for the expansion of the range of target pests and the appropriate time for pest control, or for dose reduction, the agricultural and horticultural insecticide of the present invention can be used after mixed with other agricultural and horticultural insecticides, acaricides, nematicides, microbicides, biopesticides and/or the like. Further, the agricultural and horticultural insecticide can be used after mixed with herbicides, plant growth regulators, fertilizers and/or the like depending on the situation.

Examples of such additional agricultural and horticultural insecticides, acaricides and nematicides used for the above-mentioned purposes include 3,5-xylyl methylcarbamate (XMC), crystalline protein toxins produced by *Bacillus thuringiensis* such as *Bacillus thuringiensis aizawai*, *Bacillus thuringiensis israelensis*, *Bacillus thuringiensis japonensis*, *Bacillus thuringiensis kurstaki* and *Bacillus thuringiensis tenebrionis*, BPMC, Bt toxin-derived insecticidal compounds, CPCBS (chlorfenson), DCIP (dichlorodiisopropyl ether), D-D (1,3-dichloropropene), DDT, NAC, O-4-dimethylsulfamoylphenyl O,O-diethyl phosphorothioate (DSP), O-ethyl O-4-nitrophenyl phenylphosphonothioate (EPN), tripropylisocyanurate (TPIC), acrinathrin, azadirachtin, azinphos-methyl, acequinocyl, acetamiprid, acetoprole, acephate, abamectin, avermectin-B, amidoflumet, amitraz, alanycarb, aldicarb, aldoxycarb, aldrin, alpha-endosulfan, alpha-cypermethrin, albendazole, allethrin, isazofos, isamidofos, isoamidofos isoxathion, isofenphos, isoprocarb (MIPC), ivermectin, imicyafos, imidacloprid, imiprothrin, indoxacarb, esfenvalerate, ethiofencarb, ethion, ethiprole, etoxazole, ethofenprox, ethoprophos, etrimfos, emamectin, emamectin-benzoate, endosulfan, empenthrin, oxamyl, oxydemeton-methyl, oxydeprofos (ESP), oxibendazole, oxfendazole, potassium oleate, sodium oleate, cadusafos, cartap, carbaryl, carbosulfan, carbofuran, gamma-cyhalothrin, xylylcarb, quinalphos, kinoprene, chinomethionat, cloethocarb, clothianidin, clofentezine, chromafenozide, chlorantraniliprole, chlorethoxyfos, chlordimeform, chlordane, chlorpyrifos, chlorpyrifos-methyl, chlorphenapyr, chlorfenson, chlorfenvinphos, chlorfluazuron, chlorobenzilate, chlorobenzoate, kelthane (dicofol), salithion, cyanophos (CYAP), diafenthiuron, diamidafos, cyantraniliprole, theta-cypermethrin, dienochlor, cyenopyrafen, dioxabenzofos, diofenolan, sigma-cypermethrin, dichlofenthion (ECP), cycloprothrin, dichlorvos (DDVP), disulfoton, dinotefuran, cyhalothrin, cyphenothrin, cyfluthrin, diflubenzuron, cyflumetofen, diflovidazin, cyhexatin, cypermethrin, dimethylvinphos, dimethoate, dimefluthrin, silafluofen, cyromazine, spinetoram, spinosad, spirodiclofen, spirotetramat, spiromesifen, sulfluramid, sulprofos, sulfoxaflor, zeta-cypermethrin, diazinon, tau-fluvalinate, dazomet, thiacloprid, thiamethoxam, thiodicarb, thiocyclam, thiosultap, thiosultap-sodium, thionazin, thiometon, deet, dieldrin, tetrachlorvinphos, tetradifon, tetramethylfluthrin, tetramethrin, tebupirimfos, tebufenozide, tebufenpyrad, tefluthrin, teflubenzuron, demeton-S-methyl, temephos, deltamethrin, terbufos, tralopyril, tralomethrin, transfluthrin, triazamate, triazuron, trichlamide, trichlorphon (DEP), triflumuron, tolfenpyrad, naled (BRP), nithiazine, nitenpyram, novaluron, noviflumuron, hydroprene, vaniliprole, vamidothion, parathion, parathion-methyl, halfenprox, halofenozide, bistrifluron, bisultap, hydramethylnon, hydroxy propyl starch, binapacryl, bifenazate, bifenthrin, pymetrozine, pyraclofos, pyrafluprole, pyridafenthion, pyridaben, pyridalyl, pyrifluquinazon, pyriprole, pyriproxyfen, pirimicarb, pyrimidifen, pirimiphos-methyl, pyrethrins, fipronil, fenazaquin, fenamiphos, bromopropylate, fenitrothion (MEP), fenoxycarb, fenothiocarb, phenothrin, fenobucarb, fensulfothion, fenthion (MPP), phenthoate (PAP), fenvalerate, fenpyroximate, fenpropathrin, fenbendazole, fosthiazate, formetanate, butathiofos, buprofezin, furathiocarb, prallethrin, fluacrypyrim, fluazinam, fluazuron, fluensulfone, flucycloxuron, flucythrinate, fluvalinate, flupyrazofos, flufenerim, flufenoxuron, flufenzine, flufenprox, fluproxyfen, flubrocythrinate, flubendiamide, flumethrin, flurimfen, prothiofos, protrifenbute, flonicamid, propaphos, propargite (BPPS), profenofos, profluthrin, propoxur (PHC), bromopropylate, beta-cyfluthrin, hexaflumuron, hexythiazox, heptenophos, permethrin, benclothiaz, bendiocarb, bensultap, benzoximate, benfuracarb, phoxim, phosalone, fosthiazate, fosthietan, phosphamidon, phosphocarb, phosmet (PMP), polynactins, formetanate, formothion, phorate, machine oil, malathion, milbemycin, milbemycin-A, milbemectin, mecarbam, mesulfenfos, methomyl, metaldehyde, metaflumizone, methamidophos, metam-ammonium, metam-sodium, methiocarb, methidathion (DMTP), methylisothiocyanate, methylneodecanamide, methylparathion, metoxadiazone, methoxychlor, methoxyfenozide, metofluthrin, methoprene, metolcarb, meperfluthrin, mevinphos, monocrotophos, monosultap, lambda-cyhalothrin, ryanodine, lufenuron, resmethrin, lepimectin, rotenone, levamisole hydrochloride, fenbutatin oxide, morantel tartarate, methyl bromide, tricyclohexyltin hydroxide (cyhexatin), calcium cyanamide, calcium polysulfide, sulfur and nicotine-sulfate.

Exemplary agricultural and horticultural microbicides used for the same purposes as above include aureofungin, azaconazole, azithiram, acypetacs, acibenzolar, acibenzolar-S-methyl, azoxystrobin, anilazine, amisulbrom, ampropylfos, ametoctradin, allyl alcohol, aldimorph, amobam, isotianil, isovaledione, isopyrazam, isoprothiolane, ipconazole, iprodione, iprovalicarb, iprobenfos, imazalil, iminoctadine, iminoctadine-albesilate, iminoctadine-triacetate, imibenconazole, uniconazole, uniconazole-P, echlomezole, edifenphos, etaconazole, ethaboxam, ethirimol, etem, ethoxyquin, etridiazole, enestroburin, epoxiconazole, oxadixyl, oxycarboxin, copper-8-quinolinolate, oxytetracycline, copper-oxinate, oxpoconazole, oxpoconazole-fumarate, oxolinic acid, octhilinone, ofurace, orysastrobin, metam-sodium, kasugamycin, carbamorph, carpropamid, carbendazim, carboxin, carvone, quinazamid, quinacetol, quinoxyfen, quinomethionate, captafol, captan, kiralaxyl, quinconazole, quintozene, guazatine, cufraneb, cuprobam, glyodin, griseofulvin, climbazole, cresol, kresoxim-methyl, chlozolinate, clotrimazole, chlobenthiazone, chloraniformethan, chloranil, chlorquinox, chloropicrin, chlorfenazole, chlorodinitronaphthalene, chlorothalonil, chloroneb, zarilamid, salicylanilide, cyazofamid, diethyl pyrocarbonate, diethofencarb, cyclafuramid, diclocymet, dichlozoline, diclobutrazol, dichlofluanid, cycloheximide, diclomezine, dicloran, dichlorophen, dichlone, disulfiram, ditalimfos, dithianon, diniconazole, diniconazole-M, zineb, dinocap, dinocton, dinosulfon, dinoterbon, dinobuton, dinopenton, dipyrithione, diphenylamine, difenoconazole, cyflufenamid, diflumetorim, cyproconazole, cyprodinil, cyprofuram, cypendazole, simeconazole, dimethirimol, dimethomorph, cymoxanil, dimoxystrobin, methyl bromide, ziram, silthiofam, streptomycin, spiroxamine, sultropen, sedaxane, zoxamide, dazomet, thiadiazin, tiadinil, thiadifluor, thiabendazole, tioxymid, thiochlorfenphim, thiophanate, thiophanate-methyl, thicyofen, thioquinox, chinomethionat, thifluzamide, thiram, decafentin, tecnazene, tecloftalam, tecoram, tetraconazole, debacarb, dehydroacetic acid, tebuconazole, tebufloquin, dodicin, dodine, dodecyl benzensulfonate bis-ethylene diamine copper(II) (DBEDC), dodemorph, drazoxolon, triadimenol, triadimefon, triazbutil, triazoxide, triamiphos, triarimol, trichlamide, tricyclazole, triticonazole, tridemorph, tributyltin oxide, triflumizole, trifloxystrobin, triforine, tolylfluanid, tolclofos-methyl, natamycin, nabam, nitrothal-isopropyl, nitrostyrene, nuarimol, copper nonylphenol sulfonate, halacrinate, validamycin, valifenalate, harpin protein, bixafen, picoxystrobin, picobenzamide, bithionol, bitertanol, hydroxyisoxazole, hydroxyisoxazole-potassium, binapacryl, biphenyl, piperalin, hymexazol, pyraoxystrobin, pyracarbolid, pyraclostrobin, pyrazophos, pyrametostrobin, pyriofenone, pyridinitril, pyrifenox, pyribencarb, pyrimethanil, pyroxychlor, pyroxyfur, pyroquilon, vinclozolin, famoxadone, fenapanil, fenamidone, fenaminosulf, fenarimol, fenitropan, fenoxanil, ferimzone, ferbam, fentin, fenpiclonil, fenpyrazamine, fenbuconazole, fenfuram, fenpropidin, fenpropimorph, fenhexamid, phthalide, buthiobate, butylamine, bupirimate, fuberidazole, blasticidin-S, furametpyr, furalaxyl, fluacrypyrim, fluazinam, fluoxastrobin, fluotrimazole, fluopicolide, fluopyram, fluoroimide, furcarbanil, fluxapyroxad, fluquinconazole, furconazole, furconazole-cis, fludioxonil, flusilazole, flusulfamide, flutianil, flutolanil, flutriafol, furfural, furmecyclox, flumetover, flumorph, proquinazid, prochloraz, procymidone, prothiocarb, prothioconazole, propamocarb, propiconazole, propineb, furophanate, probenazole, bromuconazole, hexachlorobutadiene, hexaconazole, hexylthiofos, bethoxazin, benalaxyl, benalaxyl-M, benodanil, benomyl, pefurazoate, benquinox, penconazole, benzamorf, pencycuron, benzohydroxamic acid, bentaluron, benthiazole, benthiavalicarb-isopropyl, penthiopyrad, penflufen, boscalid, phosdiphen, fosetyl, fosetyl-Al, polyoxins, polyoxorim, polycarbamate, folpet, formaldehyde, machine oil, maneb, mancozeb, mandipropamid, myclozolin, myclobutanil, mildiomycin, milneb, mecarbinzid, methasulfocarb, metazoxolon, metam, metam-sodium, metalaxyl, metalaxyl-M, metiram, methyl isothiocyanate, meptyldinocap, metconazole, metsulfovax, methfuroxam, metominostrobin, metrafenone, mepanipyrim, mefenoxam, meptyldinocap, mepronil, mebenil, iodomethane, rabenzazole, benzalkonium chloride, basic copper chloride, basic copper sulfate, inorganic microbicides such as silver, sodium hypochlorite, cupric hydroxide, wettable sulfur, calcium polysulfide, potassium hydrogen carbonate, sodium hydrogen carbonate, sulfur, copper sulfate anhydride, nickel dimethyldithiocarbamate, copper compounds such as copper-8-quinolinolate (oxine copper), zinc sulfate and copper sulfate pentahydrate.

Exemplary herbicides used for the same purposes as above include 1-naphthylacetamide, 2,4-PA, 2,3,6-TBA, 2,4,5-T, 2,4,5-TB, 2,4-D, 2,4-DB, 2,4-DEB, 2,4-DEP, 3,4-

DA, 3,4-DB, 3,4-DP, 4-CPA, 4-CPB, 4-CPP, MCP, MCPA, MCPA-thioethyl, MCPB, ioxynil, aclonifen, azafenidin, aciflurofen, aziprotryne, azimsulfuron, asulam, acetochlor, atrazine, atraton, anisuron, anilofos, aviglycine, abscisic acid, amicarbazone, amidosulfuron, amitrole, aminocyclopyrachlor, aminopyralid, amibuzin, amiprophos-methyl, ametridione, ametryn, alachlor, allidochlor, alloxydim, alorac, isouron, isocarbamid, isoxachlortole, isoxapyrifop, isoxaflutole, isoxaben, isocil, isonoruron, isoproturon, isopropalin, isopolinate, isomethiozin, inabenfide, ipazine, ipfencarbazone, iprymidam, imazaquin, imazapic, imazapyr, imazamethapyr, imazamethabenz, imazamethabenz-methyl, imazamox, imazethapyr, imazosulfuron, indaziflam, indanofan, indolebutyric acid, uniconazole-P, eglinazine, esprocarb, ethametsulfuron, ethametsulfuron-methyl, ethalfluralin, ethiolate, ethychlozate-ethyl, ethidimuron, etinofen, ethephon, ethoxysulfuron, ethoxyfen, etnipromid, ethofumesate, etobenzanid, epronaz, erbon, endothal, oxadiazon, oxadiargyl, oxaziclomefone, oxasulfuron, oxapyrazon, oxyfluorfen, oryzalin, orthosulfamuron, orbencarb, cafenstrole, cambendichlor, carbasulam, carfentrazone, carfentrazone-ethyl, karbutilate, carbetamide, carboxazole, quizalofop, quizalofop-P, quizalofop-ethyl, xylachlor, quinoclamine, quinonamid, quinclorac, quinmerac, cumyluron, cliodinate, glyphosate, glufosinate, glufosinate-P, credazine, clethodim, cloxyfonac, clodinafop, clodinafop-propargyl, chlorotoluron, clopyralid, cloproxydim, cloprop, chlorbromuron, clofop, clomazone, chlomethoxynil, chlomethoxyfen, clomeprop, chlorazifop, chlorazine, cloransulam, chloranocryl, chloramben, cloransulam-methyl, chloridazon, chlorimuron, chlorimuron-ethyl, chlorsulfuron, chlorthal, chlorthiamid, chlortoluron, chlornitrofen, chlorfenac, chlorfenprop, chlorbufam, chlorflurazole, chlorflurenol, chlorprocarb, chlorpropham, chlormequat, chloreturon, chloroxynil, chloroxuron, chloropon, saflufenacil, cyanazine, cyanatryn, diallate, diuron, diethamquat, dicamba, cycluron, cycloate, cycloxydim, diclosulam, cyclosulfamuron, dichlorprop, dichlorprop-P, dichlobenil, diclofop, diclofop-methyl, dichlormate, dichloralurea, diquat, cisanilide, disul, siduron, dithiopyr, dinitramine, cinidon-ethyl, dinosam, cinosulfuron, dinoseb, dinoterb, dinofenate, dinoprop, cyhalofop-butyl, diphenamid, difenoxuron, difenopten, difenzoquat, cybutryne, cyprazine, cyprazole, diflufenican, diflufenzopyr, dipropetryn, cypromid, cyperquat, gibberellin, simazine, dimexano, dimethachlor, dimidazon, dimethametryn, dimethenamid, simetryn, simeton, dimepiperate, dimefuron, cinmethylin, swep, sulglycapin, sulcotrione, sulfallate, sulfentrazone, sulfosulfuron, sulfometuron, sulfometuron-methyl, secbumeton, sethoxydim, sebuthylazine, terbacil, daimuron, dazomet, dalapon, thiazafluron, thiazopyr, thiencarbazone, thiencarbazone-methyl, tiocarbazil, tioclorim, thiobencarb, thidiazimin, thidiazuron, thifensulfuron, thifensulfuron-methyl, desmedipham, desmetryn, tetrafluron, thenylchlor, tebutam, tebuthiuron, terbumeton, tepraloxydim, tefuryltrione, tembotrione, delachlor, terbacil, terbucarb, terbuchlor, terbuthylazine, terbutryn, topramezone, tralkoxydim, triaziflam, triasulfuron, tri-allate, trietazine, tricamba, triclopyr, tridiphane, tritac, tritosulfuron, triflusulfuron, triflusulfuron-methyl, trifluralin, trifloxysulfuron, tripropindan, tribenuron-methyl, tribenuron, trifop, trifopsime, trimeturon, naptalam, naproanilide, napropamide, nicosulfuron, nitralin, nitrofen, nitrofluorfen, nipyraclofen, neburon, norflurazon, noruron, barban, paclobutrazol, paraquat, paraflufen, haloxydine, haloxyfop, haloxyfop-P, haloxyfop-methyl, halosafen, halosulfuron, halosulfuron-methyl, picloram, picolinafen, bicyclopyrone, bispyribac, bispyribac-sodium, pydanon, pinoxaden, bifenox, piperophos, hymexazol, pyraclonil, pyrasulfotole, pyrazoxyfen, pyrazosulfuron, pyrazosulfuron-ethyl, pyrazolate, bilanafos, pyraflufen-ethyl, pyriclor, pyridafol, pyrithiobac, pyrithiobac-sodium, pyridate, pyriftalid, pyributicarb, pyribenzoxim, pyrimisulfan, primisulfuron, pyriminobac-methyl, pyroxasulfone, pyroxsulam, fenasulam, phenisopham, fenuron, fenoxasulfone, fenoxaprop, fenoxaprop-P, fenoxaprop-ethyl, phenothiol, fenoprop, phenobenzuron, fenthiaprop, fenteracol, fentrazamide, phenmedipham, phenmedipham-ethyl, butachlor, butafenacil, butamifos, buthiuron, buthidazole, butylate, buturon, butenachlor, butroxydim, butralin, flazasulfuron, flamprop, furyloxyfen, prynachlor, primisulfuron-methyl, fluazifop, fluazifop-P, fluazifop-butyl, fluazolate, fluroxypyr, fluothiuron, fluometuron, fluoroglycofen, flurochloridone, fluorodifen, fluoronitrofen, fluoromidine, flucarbazone, flucarbazone-sodium, fluchloralin, flucetosulfuron, fluthiacet, fluthiacet-methyl, flupyrsulfuron, flufenacet, flufenican, flufenpyr, flupropacil, flupropanate, flupoxam, flumioxazin, flumiclorac, flumiclorac-pentyl, flumipropyn, flumezin, fluometuron, flumetsulam, fluridone, flurtamone, fluroxypyr, pretilachlor, proxan, proglinazine, procyazine, prodiamine, prosulfalin, prosulfuron, prosulfocarb, propaquizafop, propachlor, propazine, propanil, propyzamide, propisochlor, prohydrojasmon, propyrisulfuron, propham, profluazol, profluralin, prohexadione-calcium, propoxycarbazone, propoxycarbazone-sodium, profoxydim, bromacil, brompyrazon, prometryn, prometon, bromoxynil, bromofenoxim, bromobutide, bromobonil, florasulam, hexachloroacetone, hexazinone, pethoxamid, benazolin, penoxsulam, pebulate, beflubutamid, vernolate, perfluidone, bencarbazone, benzadox, benzipram, benzylaminopurine, benzthiazuron, benzfendizone, bensulide, bensulfuron-methyl, benzoylprop, benzobicyclon, benzofenap, benzofluor, bentazone, pentanochlor, benthiocarb, pendimethalin, pentoxazone, benfluralin, benfuresate, fosamine, fomesafen, foramsulfuron, forchlorfenuron, maleic hydrazide, mecoprop, mecoprop-P, medinoterb, mesosulfuron, mesosulfuron-methyl, mesotrione, mesoprazine, methoprotryne, metazachlor, methazole, metazosulfuron, methabenzthiazuron, metamitron, metamifop, metam, methalpropalin, methiuron, methiozolin, methiobencarb, methyldymron, metoxuron, metosulam, metsulfuron, metsulfuron-methyl, metflurazon, metobromuron, metobenzuron, methometon, metolachlor, metribuzin, mepiquat-chloride, mefenacet, mefluidide, monalide, monisouron, monuron, monochloroacetic acid, monolinuron, molinate, morfamquat, iodosulfuron, iodosulfuron-methyl-sodium, iodobonil, iodomethane, lactofen, linuron, rimsulfuron, lenacil, rhodethanil, calcium peroxide and methyl bromide.

Exemplary biopesticides used for the same purposes as above include viral formulations such as nuclear polyhedrosis viruses (NPV), granulosis viruses (GV), cytoplasmic polyhedrosis viruses (CPV) and entomopox viruses (EPV); microbial pesticides used as an insecticide or a nematicide, such as *Monacrosporium phymatophagum, Steinernema carpocapsae, Steinernema kushidai* and *Pasteuria penetrans*; microbial pesticides used as a microbicide, such as *Trichoderma lignorum, Agrobacterium radiobactor, avirulent Erwinia carotovora* and *Bacillus subtilis*; and biopesticides used as a herbicide, such as *Xanthomonas campestris*. Such a combined use of the agricultural and horticultural insecticide of the present invention with the foregoing biopesticide as a mixture can be expected to provide the same effect as above.

Other examples of the biopesticides include natural predators such as *Encarsia formosa, Aphidius colemani, Aphidoletes aphidimyza, Diglyphus isaea, Dacnusa sibirica, Phytoseiulus persimilis, Amblyseius cucumeris* and *Orius sauteri*; microbial pesticides such as *Beauveria brongniartii*; and pheromones such as (Z)-10-tetradecenyl acetate, (E,Z)-4,10-tetradecadienyl acetate, (Z)-8-dodecenyl acetate, (Z)-11-tetradecenyl acetate, (Z)-13-icosen-10-one and 14-methyl-1-octadecene.

Hereinafter, the production examples of representative benzoxazole compounds of the present invention and their intermediates will be described in more detail, but the present invention is not limited only to these examples.

Production Example 1-1

Production Method of 5-Cyclopropyl-3-ethylthio-N-(2-hydroxy-5-(trifluoromethylthio)phenyl)-2-pyridine Carboxylic Acid Amide

[Chem. 6]

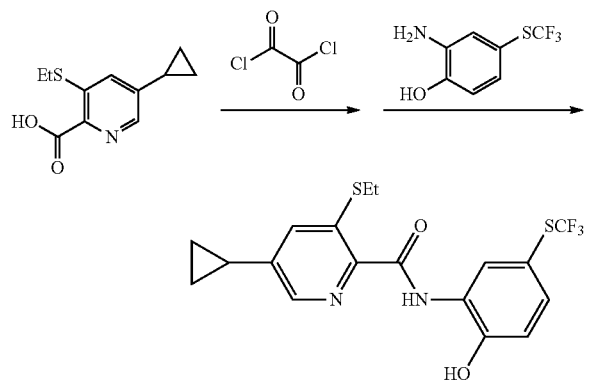

3-Ethylthio-5-cyclopropyl picolinic acid (0.9 g, 4.0 mmol) was dissolved in THF (5 mL), and oxalyl chloride (0.56 g, 1.1 Eq) was added dropwise. The mixture was stirred at room temperature for 3 hours and then concentrated to give a residue (0.97 g). A THF (3 mL) solution of the residue (200 mg) was added dropwise to a THF (5 mL) solution of 2-amino-4-(trifluoromethylthio)phenol (150 mg, 0.8 mmol) and triethylamine (0.15 g, 2 Eq) prepared in another reaction vessel. The mixture was stirred at room temperature for 1 hour. To this, 1 N HCl was added, and ethyl acetate extraction was performed. The extract was dried over anhydrous sodium sulfate and then concentrated. The resulting residue was subjected to silica gel column chromatography to give the title compound (230 mg). Yield: 77% (two steps)

Production Example 1-2

Production Method of 2-(5-Cyclopropyl-3-ethylthiopyridin-2-yl)-5-(trifluoromethylthio)benzo[d]oxazole

[Chem. 7]

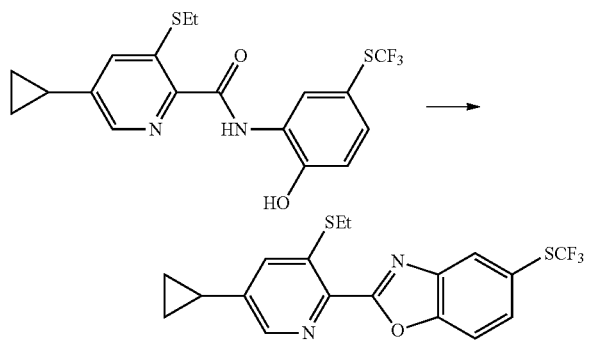

To a THF (10 mL) solution of 5-cyclopropyl-3-ethylthio-N-(2-hydroxy-5-(trifluoromethylthio)phenyl)-2-pyridine carboxylic acid amide (120 mg, 0.48 mmol) and triphenylphosphine (151 mg, 2 Eq), DMEAD (135 mg, 2 Eq) was added. The mixture was stirred at room temperature for 1 hour and then concentrated. The resulting residue was subjected to silica gel column chromatography to give the title compound (89 mg).

Yield: 78%

Production Example 1-3

Production Method of 2-(5-Cyclopropyl-3-ethylsulfonyl pyridin-2-yl)-5-(trifluoromethylsulfinyl)benzo[d]oxazole (Compound Number 1-12)

[Chem. 8]

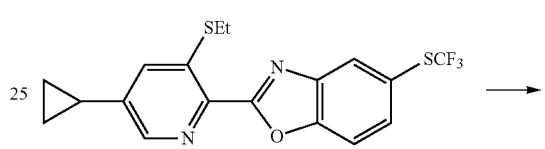

To an ethyl acetate (5 mL) solution of 2-(5-cyclopropyl-3-ethylthiopyridin-2-yl)-5-(trifluoromethylthio)benzo[d]oxazole (120 mg, 0.28 mmol), 65% mCPBA (m-chloroperoxybenzoic acid) (150 mg, 2 Eq) was added. The mixture was stirred at room temperature overnight. To this, FAMSO (formaldehyde dimethyl dithioacetal S-oxide) and triethylamine were successively added. The reaction mixture was concentrated, and the resulting residue was subjected to silica gel column chromatography to give the title compound (44 mg).

Yield: 37%

Physical property: Melting point 58 to 60° C.

Production Example 2

Production Method of 2-(5-Cyclopropyl-3-ethylsulfonyl pyridin-2-yl)-5-(trifluoromethoxy)benzo[d]oxazole (Compound Number 1-3)

The title compound was obtained in the same manner as described in Production Examples 1-1 to 1-3 except that 2-amino-4-(trifluoromethoxy)phenol was used instead of 2-amino-4-(trifluoromethylthio)phenol.

Physical property: Melting point 113 to 114° C.

Reference Example 1

Production Method of 5-Chloro-6-ethoxycarbonyl Nicotinic Acid

[Chem. 9]

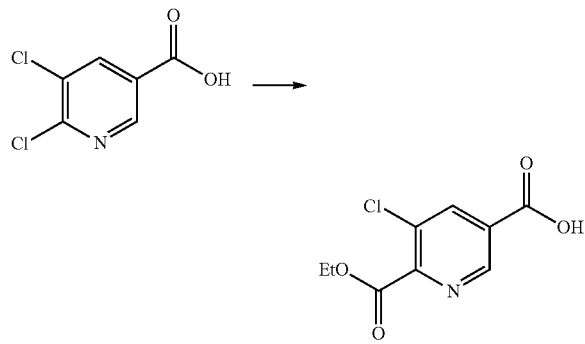

An autoclave was charged with an ethanol (60 mL) solution of 5,6-dichloronicotinic acid (10 g, 52 mmol). To this, DPPB (1,4-bis(diphenylphosphino)butane) (2.2 g, 10 mol %), triethylamine (14 g, 2.5 Eq) and $PdCl_2(PPh_3)_2$ (911 mg, 2.5 mol %) were added. The atmosphere in the reaction system was replaced with carbon monoxide (CO pressure, 4.0 MPa), and the mixture was stirred at 135° C. for 4 hours. To the reaction mixture, water and 3 N hydrochloric acid were added to acidify the aqueous layer, and ethyl acetate extraction was performed several times. The organic layer was dried over sodium sulfate and then concentrated, and the solid residue was washed with a hexane-ethyl acetate (2:1 (v/v)) mixture to give the desired compound 5-chloro-6-ethoxycarbonyl nicotinic acid (10.9 g).

Yield: 76%

Physical property: $^1$H-NMR ($CDCl_3$) δ 9.02 (d, 1H), 8.44 (d, 1H), 4.42 (dd, 2H), 1.33 (t, 3H)

Reference Example 2

Production Method of 5-Chloro-6-ethoxycarbonyl Nicotinic Acid t-Butyl Ester

[Chem. 10]

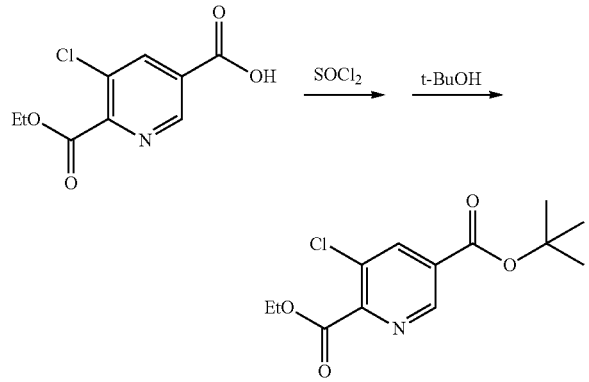

The 5-chloro-6-ethoxycarbonyl nicotinic acid (10.9 g, 47.6 mmol) obtained in Reference Example 1 was dissolved in toluene (30 mL), and DMF (N,N-dimethylformamide) (4 mL) was added to the solution. Next, thionyl chloride (11 g, 2 Eq) was added, and the mixture was heated at 90° C. with stirring for 3 hours. The reaction mixture was allowed to come to room temperature and then concentrated. In another vessel, a mixture of t-butanol (35 mL, 10 Eq), THF (100 mL), diisopropylethylamine (50 mL, 7 Eq) and DMAP (4-dimethylaminopyridine) (6 g, 1 Eq) was prepared, and to this, the concentrated residue was slowly added under ice cooling. The reaction mixture was heated under reflux for 3 hours and then allowed to cool down to room temperature. To this, water and ethyl acetate were added, and extraction was performed several times. The organic layer was dried over sodium sulfate and then concentrated. The resulting crude product was subjected to silica gel column chromatography to give the title compound (8.43 g).

Yield: 62%

Physical property: $^1$H-NMR ($CDCl_3$) δ 9.05 (d, 1H), 8.30 (d, 1H), 4.50 (dd, 2H), 1.61 (s, 9H), 1.44 (t, 3H)

Reference Example 3

Production Method of 5-Ethylthio-6-ethoxycarbonyl Nicotinic Acid t-Butyl Ester

[Chem. 11]

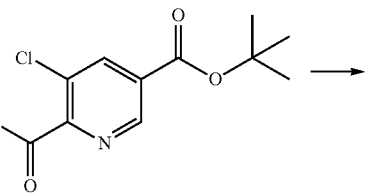

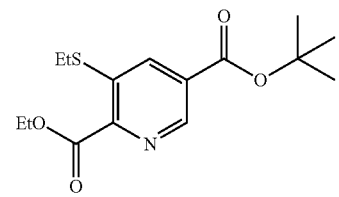

5-Chloro-6-ethoxycarbonyl nicotinic acid t-butyl ester (8.43 g, 21.65 mmol) was dissolved in DMF (100 mL). To the solution, sodium ethanethiolate (2.27 g, 1 Eq) was slowly added under ice cooling, and the mixture was stirred for 5 minutes. To this, water and 0.5 N hydrochloric acid were successively added. After ethyl acetate extraction was performed several times, the organic layer was dried over sodium sulfate and then concentrated. The resulting crude product was subjected to silica gel column chromatography to give the title compound (6.17 g).

Yield: 92%

Physical property: $^1$H-NMR ($CDCl_3$) δ 8.91 (d, 1H), 8.22 (d, 1H), 4.49 (dd, 2H), 2.99 (dd, 2H), 1.61 (s, 9H), 1.45 (t, 3H), 1.40 (t, 3H)

Reference Example 4

Production Method of
3-Ethylthio-5-t-butoxycarbonylamino Picolinic Acid
Ethyl Ester

[Chem. 12]

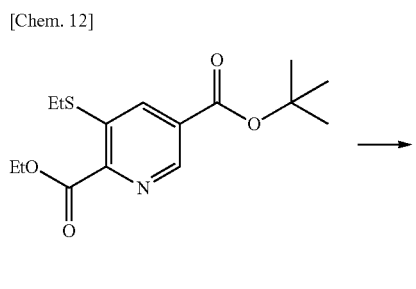

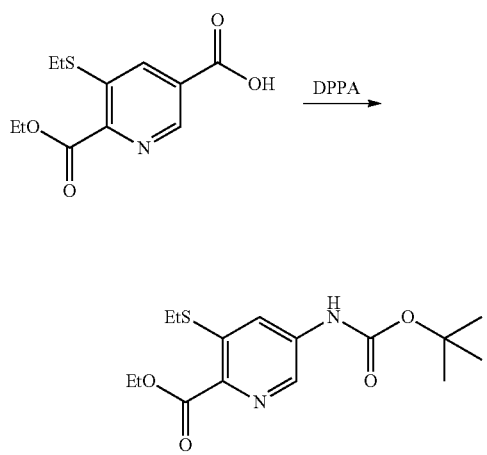

5-Ethylthio-6-ethoxycarbonyl nicotinic acid t-butoxy ester (6.17 g, 19.9 mmol) was dissolved in trifluoroacetic acid (30 mL), and the solution was heated under reflux for 30 minutes. The reaction mixture was concentrated, and toluene and ethyl acetate were added to the residue. The mixture was concentrated again to give 5-ethylthio-6-ethoxycarbonyl nicotinic acid as a crude product.

Yield: Unpurified

Physical property: $^1$H-NMR (CDCl$_3$) δ 9.06 (d, 1H), 8.33 (d, 1H), 4.52 (q, 2H), 3.03 (q, 2H), 1.50-1.41 (m, 6H)

To the crude product, t-butanol (100 mL), triethylamine (6.5 g, 3 Eq) and diphenylphosphoryl azide (11.74 g, 1.2 Eq) were added, and the mixture was stirred at room temperature for 1 hour and then refluxed for 4 hours. The reaction mixture was concentrated, and the resulting crude product was subjected to silica gel column chromatography (hexane-ethyl acetate=2:1 (v/v)) to give the title compound (3.63 g).

Yield: 56% (two steps)

Physical property: $^1$H-NMR (CDCl$_3$) δ 8.25 (d, 1H), 8.09 (d, 1H), 6.74 (s, 1H), 4.46 (dd, 2H), 2.97 (dd, 2H), 1.53 (s, 9H), 1.44 (t, 3H), 1.41 (t, 3H)

Reference Example 5

Production Method of 5-Amino-3-ethylthiopicolinic
Acid Ethyl Ester

[Chem. 13]

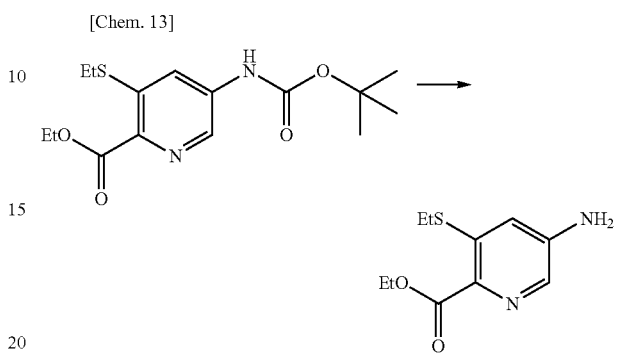

3-Ethylthio-5-t-butoxycarbonylamino picolinic acid ethyl ester (670 mg, 2.06 mmol) was dissolved in trifluoroacetic acid (30 mL), and the solution was stirred at room temperature for 30 minutes. The reaction mixture was concentrated, and water, ethyl acetate and potassium carbonate were added to the residue. After ethyl acetate extraction was performed several times, the organic layer was dried over sodium sulfate and then concentrated. The resulting crude product was subjected to silica gel column chromatography to give the title compound (358 mg).

Yield: 77%

Physical property: $^1$H-NMR (CDCl$_3$) δ 7.89 (d, 1H), 6.80 (s, 1H), 4.43 (dd, 2H), 4.08 (s, 2H), 2.88 (dd, 2H), 1.56 (s, 9H), 1.42 (t, 3H), 1.40 (t, 3H)

Reference Example 6

Production Method of 3-Ethylthio-5-iodopicolinic
Acid Ethyl Ester

[Chem. 14]

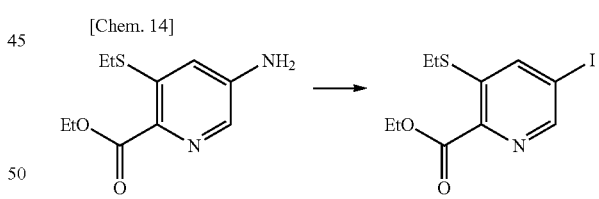

5-Amino-3-ethylthiopicolinic acid ethyl ester (1 g, 4.44 mmol) was dissolved in acetonitrile (10 mL). To the solution, trifluoroacetic acid (500 mg, 1 Eq) and p-toluenesulfonic acid (2.6 g, 3 Eq) were added, and the mixture was cooled in a water bath at about 5° C. To the reaction mixture, an aqueous solution (10 mL) of potassium iodide (2.25 g, 3 Eq) and sodium nitrite (612 mg, 2 Eq) prepared in another vessel was slowly added. The mixture was stirred for 30 minutes and further stirred at room temperature for 30 minutes. To the reaction mixture, an aqueous "hypo" (sodium hyposulfite) solution was added. After ethyl acetate extraction was performed several times, the organic layer was dried and then concentrated. The resulting crude product was subjected to silica gel column chromatography to give the title compound (761 mg).

Yield: 51%

Physical property: $^1$H-NMR (CDCl$_3$) δ 8.61 (s, 1H), 7.95 (s, 1H), 4.45 (dd, 2H), 2.91 (dd, 2H), 1.43 (t, 3H), 1.39 (t, 3H)

Reference Example 7

Production Method of 3-Ethylthio-5-cyclopropyl Picolinic Acid

[Chem. 15]

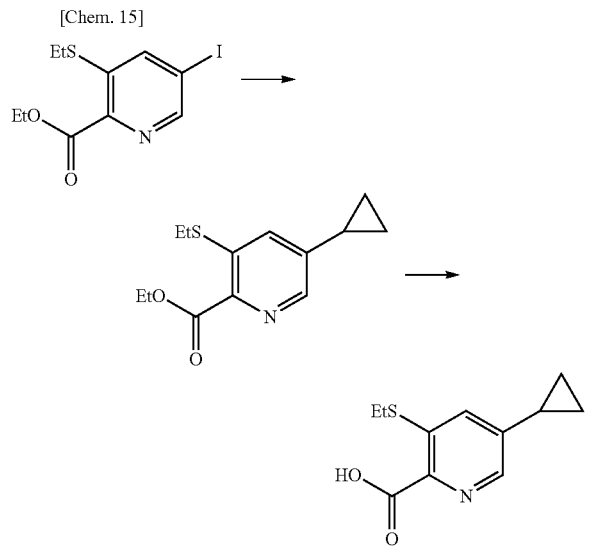

3-Ethylthio-5-iodopicolinic acid ethyl ester (2 g, 5.9 mmol), cyclopropylboronic acid (1.0 g, 2 Eq), potassium phosphate (tribasic) (6.3 g, 5 Eq) and PdCl$_2$(dppf) acetone adduct (1.0 g, 0.2 Eq) were dissolved in a mixed solvent of toluene (40 mL) and water (10 mL), and the solution was heated under reflux for 2 hours. After cooling, the reaction was quenched with 1 N HCl, and ethyl acetate extraction was performed. The extract was dried over anhydrous sodium sulfate and then concentrated. The resulting crude product was purified by silica gel column chromatography to give the title compound (1.32 g).

Yield: 89%

Physical property: $^1$H-NMR δ 8.19 (d, 1H), 7.27 (d, 1H), 4.46 (q, 2H), 2.92 (q, 2H), 1.97-1.90 (m, 1H), 1.46-1.37 (m, 6H), 1.13-1.10 (m, 2H), 0.82-0.78 (m, 2H)

3-Ethylthio-5-cyclopropyl picolinic acid ethyl ester (1.12 g, 4.5 mmol) was dissolved in ethanol (10 mL), and a 15% aqueous NaOH solution (2.4 g, 2 Eq) was added. The reaction mixture was stirred at room temperature for 3 hours, and the ethanol was evaporated off. The residue was completely dissolved in water, and 1 N HCl was added dropwise to adjust the pH to 3 to 4. The resulting solid was collected by filtration and dissolved in ethyl acetate. The solution was dried over anhydrous sodium sulfate and then concentrated to give the title compound (0.91 g).

Yield: 91%

Physical property: $^1$H-NMR δ 8.01 (d, 1H), 7.31 (d, 1H), 2.95 (q, 2H), 2.00-1.94 (m, 1H), 1.42 (t, 3H), 1.21-1.16 (m, 2H), 0.87-0.84 (m, 2H)

Hereinafter, formulation examples are shown, but the present invention is not limited thereto. In the formulation examples, the "parts" means parts by weight.

Formulation Example 1

| | |
|---|---|
| Compound of the present invention | 10 parts |
| Xylene | 70 parts |
| N-methylpyrrolidone | 10 parts |
| Equal-weight mixture of polyoxyethylene nonylphenyl ether and calcium alkylbenzene sulfonate | 10 parts |

The above ingredients are uniformly mixed for dissolution to give an emulsifiable concentrate formulation.

Formulation Example 2

| | |
|---|---|
| Compound of the present invention | 3 parts |
| Clay powder | 82 parts |
| Diatomite powder | 15 parts |

The above ingredients are uniformly mixed and then pulverized to give a dust formulation.

Formulation Example 3

| | |
|---|---|
| Compound of the present invention | 5 parts |
| Mixture of bentonite powder and clay powder | 90 parts |
| Calcium lignosulfonate | 5 parts |

The above ingredients are uniformly mixed. After addition of an appropriate volume of water, the mixture is kneaded, granulated and dried to give a granular formulation.

Formulation Example 4

| | |
|---|---|
| Compound of the present invention | 20 parts |
| Kaolin and synthetic high-dispersion silicic acid | 75 parts |
| Equal-weight mixture of polyoxyethylene nonylphenyl ether and calcium alkylbenzene sulfonate | 5 parts |

The above ingredients are uniformly mixed and then pulverized to give a wettable powder formulation.

Hereinafter, test examples in connection with the present invention are shown, but the present invention is not limited thereto.

Test Example 1

Test for Control Effect on *Myzus persicae*

Chinese cabbage plants were planted in plastic pots (diameter: 8 cm, height: 8 cm), green peach aphids (*Myzus persicae*) were propagated on the plants, and the number of surviving green peach aphids in each pot was counted. The benzoxazole compounds represented by the general formula (1) of the present invention or salts thereof were separately dispersed in water and diluted to 500 ppm. The agrochemical dispersions were applied to the foliage of the potted Chinese cabbage plants. After the plants were air-dried, the pots were kept in a greenhouse. At 6 days after the foliar application, the number of surviving green peach aphids on the Chinese cabbage plant in each pot was counted, the control rate was calculated according to the formula shown below, and the control effect was evaluated according to the criteria shown below.

$$\text{Control rate} = 100 - \{(T \times Ca)/(Ta \times C)\} \times 100 \quad \text{[Math. 1]}$$

Ta: the number of survivors before the foliar application in a treatment plot
T: the number of survivors after the foliar application in a treatment plot
Ca: the number of survivors before the foliar application in a non-treatment plot
C: the number of survivors after the foliar application in a non-treatment plot
Criteria
A: the control rate is 100%.
B: the control rate is 90 to 99%.
C: the control rate is 80 to 89%.
D: the control rate is 50 to 79%.

As a result, the compounds 1-1, 1-3 and 1-12 of the present invention showed the activity level evaluated as A.

Test Example 2

Insecticidal test on *Laodelphax striatella*

The benzoxazole compounds represented by the general formula (1) of the present invention or salts thereof were separately dispersed in water and diluted to 500 ppm. Rice plant seedlings (variety: Nihonbare) were dipped in the agrochemical dispersions for 30 seconds. After air-dried, each seedling was put into a separate glass test tube and inoculated with ten 3rd-instar larvae of *Laodelphax striatella*, and then the glass test tubes were capped with cotton plugs. At 8 days after the inoculation, the numbers of surviving larvae and dead larvae were counted, the corrected mortality rate was calculated according to the formula shown below and evaluated according to the criteria shown below.

$$\text{Corrected mortality rate (\%)} = 100 \times (\text{Survival rate in a non-treatment plot} - \text{Survival rate in a treatment plot})/\text{Survival rate in a non-treatment plot} \quad \text{[Math. 2]}$$

Criteria
A: the corrected mortality rate is 100%.
B: the corrected mortality rate is 90 to 99%.
C: the corrected mortality rate is 80 to 89%.
D: the corrected mortality rate is 50 to 79%.

As a result, the compounds 1-1, 1-3 and 1-12 of the present invention showed the activity level evaluated as A.

Test Example 3

Insecticidal test on *Plutella xylostella*

Adults of *Plutella xylostella* were released onto Chinese cabbage seedlings and allowed to lay eggs thereon. At 2 days after the release of the adults, the Chinese cabbage seedlings with laid eggs were dipped for about 30 seconds in agrochemical aqueous dispersions diluted to 500 ppm, each of which contained a different kind of benzoxazole compound represented by the general formula (1) of the present invention as an active ingredient. After air-dried, the seedlings were kept in a thermostatic chamber at 25° C. At 6 days after the dip treatment, the number of hatched larvae per plot was counted, the mortality rate was calculated according to the formula shown below, and the insecticidal effect was evaluated according to the criteria of Test Example 2. This test was conducted in triplicate using 10 adults of *Plutella xylostella* per plot.

$$\text{Corrected mortality rate (\%)} = 100 \times (\text{Number of hatched larvae in a non-treatment plot} - \text{Number of hatched larvae in a treatment plot})/\text{Number of hatched larvae in a non-treatment plot} \quad \text{[Math. 3]}$$

As a result, the compounds 1-1, 1-3 and 1-12 of the present invention showed the activity level evaluated as A.

INDUSTRIAL APPLICABILITY

The compound of the present invention is highly effective for the control of various pests harmful to agriculture and horticulture and thus is useful.

The invention claimed is:

1. A benzoxazole compound represented by the general formula (1):

[Chem. 1]

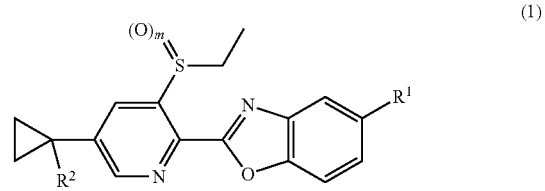

(1)

{wherein:
R$^1$ represents a halo (C$_1$-C$_3$) alkoxy group; a halo (C$_1$-C$_3$) alkylsulfinyl group; or a halo (C$_1$-C$_3$) alkylsulfonyl group,
R$^2$ represents a hydrogen atom or a cyano group, and
m represents 0; 1; or 2}
or a salt thereof.

2. The benzoxazole compound or the salt according to claim 1, wherein R$^1$ is a halo (C$_1$-C$_3$) alkoxy group.

3. The benzoxazole compound or the salt according to claim 1, wherein R$^1$ is a halo (C$_1$-C$_3$) alkylsulfinyl group.

4. An agricultural and horticultural insecticide comprising the benzoxazole compound or the salt thereof according to claim 1 as an active ingredient.

5. A method of using the agricultural and horticultural insecticide according to claim 4, the method comprising applying an effective amount of the benzoxazole compound or the salt thereof according to claim 1 to plants or soil.

6. An animal ectoparasite control agent comprising the benzoxazole compound or the salt thereof according to claim 1 as an active ingredient.

* * * * *

UNITED STATES PATENT AND TRADEMARK OFFICE
CERTIFICATE OF CORRECTION

| | | |
|---|---|---|
| PATENT NO. | : 10,575,525 B2 | |
| APPLICATION NO. | : 16/077978 | |
| DATED | : March 3, 2020 | |
| INVENTOR(S) | : Soichiro Matsuo et al. | |

It is certified that error appears in the above-identified patent and that said Letters Patent is hereby corrected as shown below:

In the Specification

In Column 2, Line 17, delete "1represents" and insert --represents--.

In Column 13, Line 55, delete "Agrotis Euproctis pseudoconspersa," and insert --Agrotis ipsilon, Euproctis pseudoconspersa,--.

In Column 14, Lines 2-3, delete "Eupoecillia ambiguella," and insert --Eupoecilia ambiguella,--.

In Column 14, Line 13, delete "Namestra brassicae," and insert --Mamestra brassicae,--.

In Column 14, Line 24, delete "Aeschynteles maculatus," and insert --Aeschynanthus maculatus,--.

In Column 14, Lines 24-25, delete "Creontiades pallidifer," and insert --Creontiades pallidus,--.

In Column 14, Line 29, delete "Stariodes iwasakii," and insert --Stariodes iwasaki,--.

In Column 14, Lines 34-35, delete "Rhopalosophum rufiabdominalis," and insert --Rhopalosiphum rufiabdominale,--.

In Column 14, Line 52, delete "Uroeucon" and insert --Uroleucon--.

In Column 14, Lines 64-65, delete "Rhopalosophum nymphaeae" and insert --Rhopalosiphum nymphaeae--.

In Column 15, Line 6, delete "triannulatus" and insert --Lineolatus--.

In Column 15, Line 6, delete "Viteus vitifolii" and insert --Viteus vitifoliae--.

Signed and Sealed this
Twenty-first Day of July, 2020

Andrei Iancu
*Director of the United States Patent and Trademark Office*

CERTIFICATE OF CORRECTION (continued)
U.S. Pat. No. 10,575,525 B2

In Column 15, Lines 23-24, delete "Aphidonuguis mali" and insert --Aphidophagous mali--.

In Column 15, Line 24, delete "Orientus ishidai" and insert --Orientus ishidae--.

In Column 15, Lines 33-34, delete "Epilachna vigintioctomaculata." and insert --Epilachna vigintioctopunctata.--.

In Column 15, Line 62, delete "Hydrellia griseola, Hydrellia griseola," and insert --Hydrellia griseola--.

In Column 16, Line 13, delete "Athalia infumata infumata," and insert --Athalia infumata,--.

In Column 16, Lines 31-32, delete "FrankLinella occidentalis," and insert --Frankliniella occidentalis,--.

In Column 16, Lines 40-41, delete "Dermacentor taiwanicus," and insert --Dermacentor taiwanensis,--.

In Column 16, Line 43, delete "Eriophyes chibaensis." and insert --Eriophyes chinensis.--.

In Column 16, Line 46, delete "Octodectes cynotis," and insert --Otodectes cynotis,--.

In Column 16, Lines 46-47, delete "Dermatophagoides ptrenyssnus," and insert --Dermatophagoides pteronyssinus,--.

In Column 16, Line 50, delete "Rhyzoglyphus robini," and insert --Rhizoglyphus robini,--.

In Column 16, Line 54, delete "flaviceps amamianus," and insert --flaviceps ammianus,--.

In Column 16, Line 54, delete "Glyptotermes kushimensis," and insert --Glyptothorax kashmirensis,--.

In Column 17, Lines 2-3, delete "Tylenchus semipenetrans;" and insert --Tylenchulus semipenetrans;--.

In Column 17, Line 6, delete "Lehmannina valentiana," and insert --Lehmannia valentiana,--.

In Column 17, Line 43, delete "Dalmalinia ovis," and insert --Damalinia ovis,--.

In Column 17, Lines 52-53, delete "Multiceps multiceps," and insert --Multiceps,--.

In Column 19, Line 48, delete "CrylAb" and insert --Cry1Ab--.

In Column 24, Line 57, delete "chlorphenapyr," and insert --chlorfenapyr--.

CERTIFICATE OF CORRECTION (continued)
U.S. Pat. No. 10,575,525 B2

In Column 25, Line 25, delete "flurimfen," and insert --flurofen,--.

In Column 26, Line 17, delete "benzensulfonate," and insert --benzenesulfonate,--.

In Column 27, Line 29, delete "chlorthal," and insert --chlorthalidone,--.

In Column 28, Line 50, delete "radiobactor," and insert --radiobacter,--.

In Column 37, Line 8, delete "plot" and insert --plot.--.

In Column 37, Line 10, delete "plot" and insert --plot.--.

In Column 37, Line 12, delete "plot" and insert --plot.--.

In Column 37, Line 14, delete "plot" and insert --plot.--.